(12) United States Patent
Lamanna et al.

(10) Patent No.: US 10,308,592 B2
(45) Date of Patent: Jun. 4, 2019

(54) NITROGEN CONTAINING HYDROFLUOROETHERS AND METHODS OF USING SAME

(71) Applicant: 3M INNOVATIVE PROPERTIES COMPANY, St. Paul, MN (US)

(72) Inventors: William M. Lamanna, Stillwater, MN (US); Michael J. Bulinski, Stillwater, MN (US); Kiah A. Smith, Mahtomedi, MN (US); Michael G. Costello, Afton, MN (US); Georgiy Teverovskiy, St. Louis Park, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 184 days.

(21) Appl. No.: 15/511,259

(22) PCT Filed: Sep. 18, 2015

(86) PCT No.: PCT/US2015/050844
§ 371 (c)(1),
(2) Date: Mar. 15, 2017

(87) PCT Pub. No.: WO2016/048808
PCT Pub. Date: Mar. 31, 2016

(65) Prior Publication Data
US 2017/0283365 A1    Oct. 5, 2017

Related U.S. Application Data

(60) Provisional application No. 62/053,855, filed on Sep. 23, 2014.

(51) Int. Cl.
| | | |
|---|---|---|
| C09K 5/04 | (2006.01) |
| C07C 217/26 | (2006.01) |
| C07D 223/04 | (2006.01) |
| C07D 241/04 | (2006.01) |
| C07D 265/30 | (2006.01) |
| C07D 207/10 | (2006.01) |
| C07D 211/38 | (2006.01) |
| C08J 9/00 | (2006.01) |
| C08J 9/14 | (2006.01) |
| C09D 7/20 | (2018.01) |
| A62D 1/00 | (2006.01) |
| C07C 211/15 | (2006.01) |
| C09K 3/00 | (2006.01) |
| C09K 5/10 | (2006.01) |
| C10M 107/38 | (2006.01) |
| C11D 3/43 | (2006.01) |
| H01L 23/46 | (2006.01) |
| H01M 10/0525 | (2010.01) |
| H01M 10/0569 | (2010.01) |
| H01B 3/24 | (2006.01) |
| H01B 3/56 | (2006.01) |

(52) U.S. Cl.
CPC .......... *C07C 217/26* (2013.01); *A62D 1/0028* (2013.01); *C07C 211/15* (2013.01); *C07D 207/10* (2013.01); *C07D 211/38* (2013.01); *C07D 223/04* (2013.01); *C07D 241/04* (2013.01); *C07D 265/30* (2013.01); *C08J 9/0028* (2013.01); *C08J 9/14* (2013.01); *C09D 7/20* (2018.01); *C09K 3/00* (2013.01); *C09K 5/048* (2013.01); *C09K 5/10* (2013.01); *C10M 107/38* (2013.01); *C11D 3/43* (2013.01); *H01L 23/46* (2013.01); *H01M 10/0525* (2013.01); *H01M 10/0569* (2013.01); *C08J 2323/04* (2013.01); *C08J 2325/04* (2013.01); *C08J 2327/06* (2013.01); *C08J 2371/10* (2013.01); *C08J 2375/04* (2013.01); *C10M 2213/0606* (2013.01); *H01B 3/24* (2013.01); *H01B 3/56* (2013.01); *H01M 2300/0034* (2013.01)

(58) Field of Classification Search
CPC ........................... C09C 217/26; C07C 211/35
See application file for complete search history.

(56) References Cited

U.S. PATENT DOCUMENTS

| | | | |
|---|---|---|---|
| 4,782,148 A | 11/1988 | Abe |
| 5,049,670 A | 9/1991 | Moore |
| 6,203,944 B1 | 3/2001 | Turner |
| 2007/0051916 A1 | 3/2007 | Flynn |
| 2007/0054186 A1 | 3/2007 | Costello |

(Continued)

FOREIGN PATENT DOCUMENTS

| | | |
|---|---|---|
| WO | 2000-003444 | 1/2004 |
| WO | 2014-120405 | 8/2014 |

OTHER PUBLICATIONS

R. E. Banks et al., Journal of the Chiemical Society, Perkin Transactions !, 1972, issue 12, pp. 1449-1452. No month available. Abstract only. (Year: 1972).*
Abe, "A New Route to Perfluorovinylamines by the Pyrolytic Reaction of an Alkali Metal Salt of Perfluoro(2-dialkylamino-propionic acids)", Chemistry Letters, 1988, pp. 1887-1890.
Abe, "An Alternative New Route to Perfluorovinylamines. Pyrolysis of an Alkali Metal Salt of Perfluoro(3-dialkylamino-propionic acids)", Chemistry Letters, 1989, pp. 905-908.

(Continued)

*Primary Examiner* — John R Hardee
(74) *Attorney, Agent, or Firm* — Adam Bramwell

(57) ABSTRACT

A hydrofluoroether compound is represented by the following general formula (1): wherein n is 1-2.

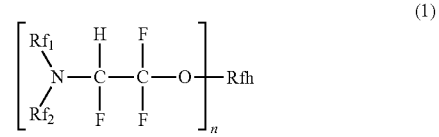

(1)

10 Claims, No Drawings

(56) References Cited

U.S. PATENT DOCUMENTS

| | | |
|---|---|---|
| 2007/0267464 A1 | 11/2007 | Vitcak |
| 2008/0139683 A1 | 6/2008 | Flynn |
| 2010/0139274 A1 | 6/2010 | Zyhowski |
| 2011/0100601 A1 | 5/2011 | Flynn |

OTHER PUBLICATIONS

Abe, "The Electrochemical Fluorination of Nitrogen-Containing Carboxylic Acids. Fluorination of Dimethylamino- or Diethylamino-Substituted Carboxylic Acid Derivatives", Journal of Fluorine Chemistry, 1990, vol. 48, pp. 257-279.

Abe, "The Electrochemical Fluorination of Nitrogen-Containing Carboxylic Acids. Fluorination of Methyl Esters of Cyclic Amino-Group Substituted Carboxylic Acids", Journal of Fluorine Chemistry, 1990, vol. 50, pp. 173-196.

Ellis, "Cleaning and Contamination of Electronics Components and Assemblies", Electrochemical Publications Limited, 1986, pp. 182-195.

Vij, "Perfluorovinyl Morpholine and Perfluorovinyl Pyrrolidine with Nucleophiles and Electrophiles", 1995, vol. 621, pp. 1865-1874.

Vij, "Perfluorovinylamines: Reactions of the Perfluorovinyl Group with Nucleophiles and Electrophiles", Inorganic Chemistry, 1993, vol. 32, No. 23, pp. 5011-5020.

International Search Report for PCT International Application No. PCT/US2015/50844, dated Dec. 14, 2015, 3 pages.

* cited by examiner

NITROGEN CONTAINING HYDROFLUOROETHERS AND METHODS OF USING SAME

CROSS REFERENCE TO RELATED APPLICATIONS

This application is a national stage filing under 35 U.S.C. 371 of PCT/US2015/050844, filed Sep. 18, 2017, which claims the benefit of U.S. Provisional Application No. 62/053,855, filed Sep. 23, 2014, the disclosure of which is incorporated by reference in its/their entirety herein.

FIELD

The present disclosure relates to nitrogen containing hydrofluoroethers and methods of making and using the same.

BACKGROUND

Various hydrofluoroether compounds are described in, for example, U.S. Published Application 2007/0051916, U.S. Published Application 2007/0054186, and in Jean'ne M. Shreeve, et. al., Z. Anorg. Allg. Chem., 621 (1995) 1865-1874.

SUMMARY

In some embodiments, a hydrofluoroether compound is provided. The hydrofluoroether compound is represented by the following general formula (1):

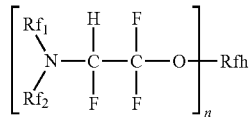

(1)

wherein n is 1-2, and each occurrence of $Rf_1$ and $Rf_2$ is:
(i) independently a linear or branched perfluoroalkyl group having 1-8 carbon and optionally comprises one or more catenated heteroatoms; or
(ii) bonded together to form a ring structure having 4-8 carbon atoms and optionally comprises one or more catenated heteroatoms; and Rfh is, when n=1, a substituted or unsubstituted, monovalent, hydrocarbon group having 1-12 carbon atoms optionally comprising one or more catenary heteroatoms and, when n=2, a substituted or unsubstituted, divalent, hydrocarbon group having 1-12 carbon atoms optionally comprising one or more catenary heteroatoms.

In some embodiments, a working fluid is provided. The working fluid includes the above-described hydrofluoroether compound. The hydrofluoroether compound is present in the working fluid at an amount of at least 50% by weight based on the total weight of the working fluid.

In some embodiments, an apparatus for heat transfer is provided. The apparatus includes a device, and a mechanism for transferring heat to or from the device. The mechanism further includes a heat transfer fluid that includes the above-described hydrofluoroether compound.

In some embodiments, a method of transferring heat is provided. The method includes providing a device and transferring heat to or from the device using a heat transfer fluid that includes the above-described hydrofluoroether compound.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

In view of an increasing demand for environmentally friendly and lox toxicity chemical compounds, it is recognized that there exists an ongoing need for new working fluids exhibiting further reductions in environmental impact and toxicity, and which can meet the performance requirements (e.g., nonflammability, solvency, and operating temperature range) of a variety of different applications (e.g., heat transfer, solvent cleaning, deposition coating solvents, and electrolyte solvents and additives), and be manufactured cost-effectively.

As used herein, "catenated heteroatom" means an atom other than carbon (for example, oxygen, nitrogen, or sulfur) that is bonded to at least two carbon atoms in a carbon chain (linear or branched or within a ring) so as to form a carbon-heteroatom-carbon linkage.

As used herein, "fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom.

As used herein, "perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

As used herein, "substituted" (in reference to a group or moiety) means that at least one carbon-bonded hydrogen atom is replaced with a halogen atom. Halogen atoms may include F, Cl, Br, and I.

As used herein, a "segregated hydrofluoroether" means a hydrofluoroether whose segments (such as alkyl or alkylene segments) linked via an ether oxygen are either perfluorinated or not fluorinated, and thus are not partially fluorinated.

As used herein, a "non-segregated hydrofluoroether" means a hydrofluoroether having one or both of the segments (such as alkyl or alkylene segments) linked via an ether oxygen that is partially fluorinated.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure is directed to hydrofluoroether compounds represented by the following general formula (1):

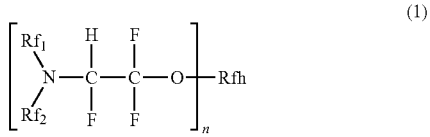

In some embodiments, n is 1-2. As can be understood with reference to general formula (1), when n=1, the hydrofluoroether compounds may be represented by the following general formula (1A), and when n=2, the hydrofluoroether compounds may be represented by the following general formula (1B):

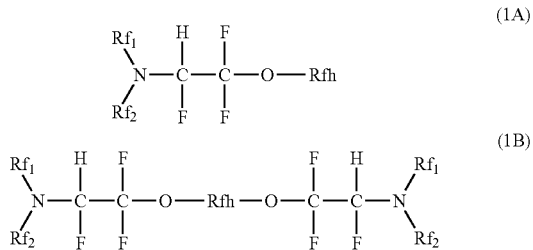

In some embodiments, each occurrence of $Rf_1$ and $Rf_2$ may be (i) independently a linear or branched perfluoralkyl group having 1-8, 1-6, or 1-4 carbon atoms and optionally comprise one or more catenated heteroatoms; or (ii) bonded together to form a ring structure having 4-8 or 4-6 carbon atoms and optionally comprise one or more catenated heteroatoms. In some embodiments, the catenated heteroatoms of the ring structure are selected from oxygen and nitrogen.

In some embodiments, when n=1, Rfh may be a monovalent, hydrocarbon group of 1-12, 1-6, or 1-3 carbon atoms that may be substituted or unsubstituted, saturated or unsaturated, linear or branched, cyclic or acyclic, and may optionally contain one or more catenanted heteroatoms.

In some embodiments, when n=2, Rfh may be a divalent, hydrocarbon group of 1-12, 2-6, or 2-4 carbon atoms that may be substituted or unsubstituted, saturated or unsaturated, linear or branched, cyclic or acyclic, and may optionally contain one or more catenated heteroatoms.

In various embodiments, the hydrogen atoms in Rfh can be partially substituted with halogen atoms. The halogen atoms may include F, Cl, Br, and I. The catenated heteroatoms may include but are not limited to N, O, and S. In some embodiments, the halogen content in the compounds of general formula (1) may be sufficient to make the hydrofluoroether non-flammable according to ASTM D-3278-96 e-1 test method ("Flash Point of Liquids by Small Scale Closed Cup Apparatus").

In some embodiments, when n=1, examples of suitable Rfh groups include —$CH_3$, —$C_2H_5$, —$C_3H_7$, —$CH_2CH$=$CH_2$, —$CH_2C$≡$CH$, —$CH_2CH_2OCH_3$, —$CH_2CF_3$, —$CH_2C_2F_5$, —$CH(CF_3)_2$, —$CH_2C_3F_7$, —$CH_2CF_2CFHCF_3$, —$CH(CH_3)CF_2CFHCF_3$, —$CH_2(CF_2CF_2)_aH$ (where a=1-3), and —$CH_2CH_2(CF_2)_bF$ (where b=1-8).

In some embodiments, when n=2, examples of suitable Rfh groups include —$CH_2CF_2CF_2CH_2$—, —$CH_2CH_2CH_2CH_2$—, —$CH_2CH$=$CHCH_2$—, and —$CH_2CH_2OCH_2CH_2$—.

In some embodiments, the hydrofluoroethers of the present disclosure may have a degree of fluorination that is at least 40%, 50%, 60%, or 70%. In other words at least 40%, 50%, 60%, or 70% of the hydrogen atoms in the hydrocarbon chain(s) are replaced by fluorine atoms.

In some embodiments, any of the above discussed catentated heteroatoms may be secondary O heteroatoms wherein the O is bonded to two carbon atoms. In some embodiments, any of the above discussed catenated heteroatoms may be tertiary N heteroatoms wherein the N is bonded to three perfluorinated carbon atoms. In some embodiments, any of the above discussed catenated heteroatoms may be secondary S heteroatoms wherein the S is bonded to two perfluorinated carbon atoms, and the remaining valences on S, if present, are occupied by F.

In various embodiments, representative examples of the compounds of general formula (1) include the following:

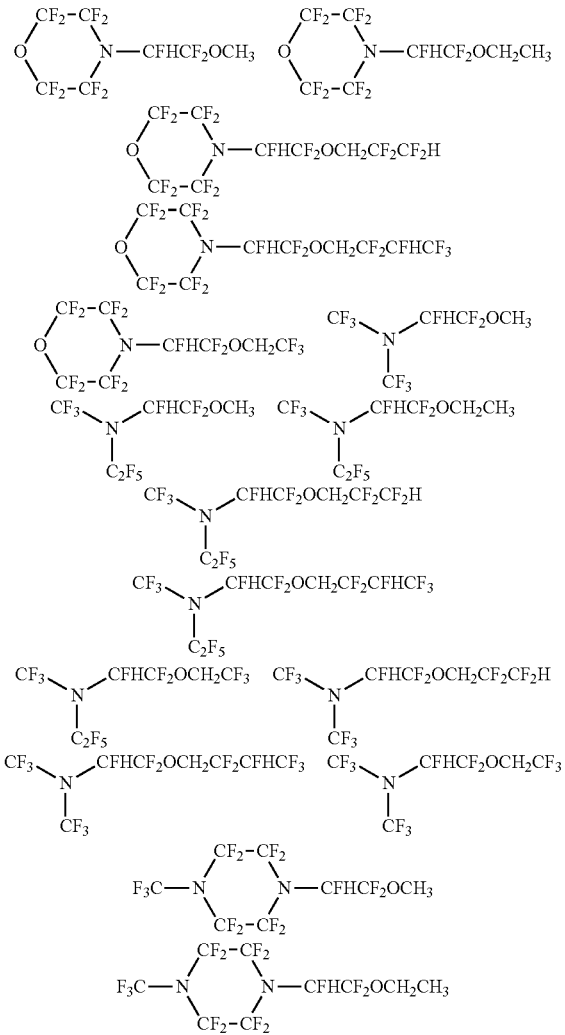

-continued

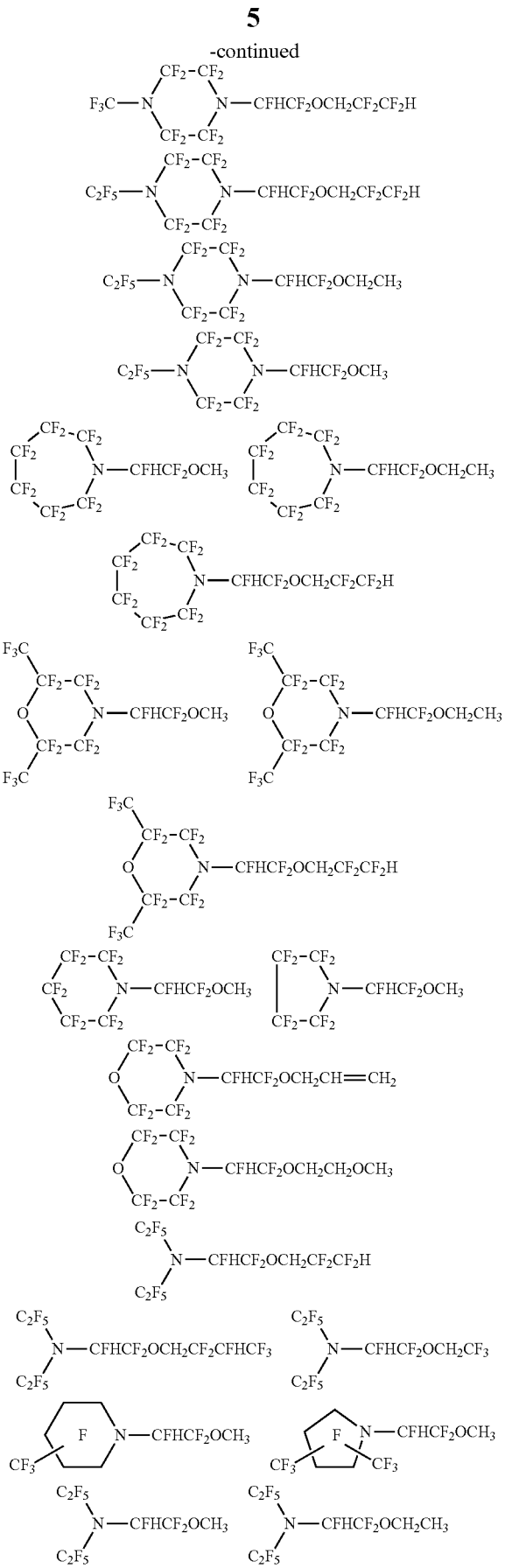

-continued

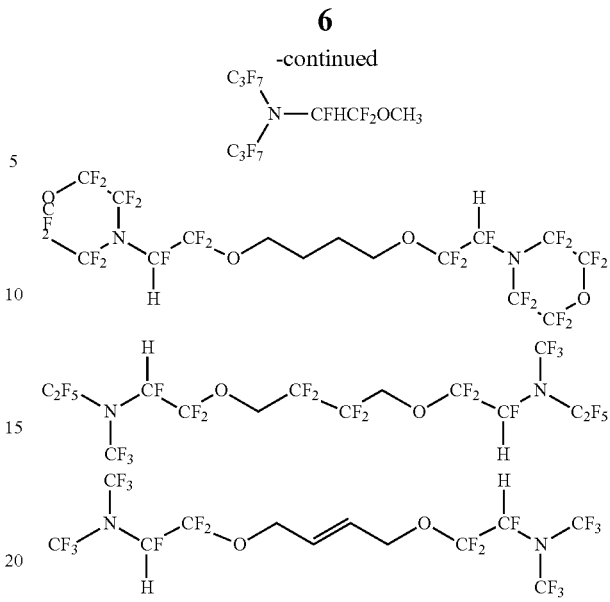

In some embodiments, the hydrofluoroether compounds of the present disclosure may be hydrophobic, relatively chemically unreactive, and thermally stable. The hydrofluoroether compounds may have a low environmental impact. In this regard, the hydrofluoroether compounds of the present disclosure may have a global warming potential (GWP) of less than 500, 300, 200, 100 or even less than 10. As used herein, GWP is a relative measure of the warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i [C(t)] dt}{\int_0^{ITH} a_{CO_2} [C_{CO_2}(t)] dt} = \frac{\int_0^{ITH} a_i C_{oi} e^{-t/\tau_i} dt}{\int_0^{ITH} a_{CO_2} [C_{CO_2}(t)] dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, $\tau$ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In some embodiments, the hydrofluoroethers of the present disclosure may be characterized as a new class of hydrofluoroethers, which have similar physical properties to that of known hydrofluoroethers (e.g., known segregated hydrofluoroethers), but which exhibit improved solvency for particular solutes (e.g., polar and nonpolar solutes) and improved miscibility with polar organic solvents and organic electrolyte formulations. Moreover, surprisingly, in accordance with some embodiments, the hydrofluoroethers of the present disclosure, which may be non-segregated hydrofluoroethers, provide low acute toxicity based on 4 hour acute inhalation or oral toxicity studies in rats (conventional wisdom has suggested that non-segregated hydrofluoroethers do not provide low toxicity). Still further, as will be discussed in further detail below, in some embodiments, the hydrofluoroethers of the present disclosure can be produced using perfluorinated vinyl amines, a relatively low cost intermediate available from the corresponding perfluorinated acid fluoride precursors.

In some embodiments, the hydrofluoroether compounds of the present disclosure can be prepared by the addition of an alcohol to a perfluorinated vinyl amine as illustrated in Scheme 1.

Scheme 1:

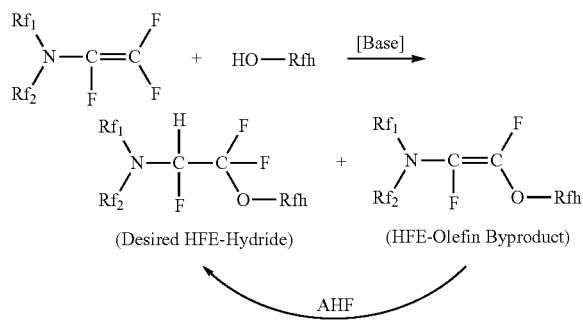

Generally, this reaction may produce the desired hydrofluoroether (or HFE-Hydride) compounds of the present disclosure as the major product, although relatively small amounts of the corresponding hydrofluoroether-olefin (or HFE-Olefin) byproduct may be produced as well. The hydrofluoroether-olefin byproduct can be readily converted back to the desired hydrofluoroether by treatment with a hydrofluorinating agent, such as anhydrous hydrogen fluoride (AHF), ultimately producing high yields of the desired hydrofluoroether compounds.

In some embodiments, the alcohol addition reaction shown in Scheme 1 can be effected by combining the perfluorinated vinyl amine starting compound and the starting alcohol in the presence of at least one basic catalyst (for example, a Lewis base). Useful catalysts include potassium carbonate, cesium carbonate, potassium fluoride, potassium hydroxide, potassium methoxide, triethylamine, trimethylamine, potassium cyanate, potassium bicarbonate, sodium carbonate, sodium bicarbonate, sodium methoxide, cesium fluoride, potassium bifluoride, potassium acetate, and the like, and mixtures thereof; with potassium carbonate, potassium bicarbonate, and mixtures thereof being preferred. A small amount of an alkali metal salt of the starting alcohol can also be used as a catalyst.

In some embodiments, the reactants and catalyst can be combined in a reactor (for example, a glass reactor or a metal pressure reactor) in any order, and the reaction can be run at a desired temperature (for example, from about −20° C. to about 75° C.) under the above described conditions with agitation. Generally, however, use of a non-reactive, polar solvent (for example, acetonitrile, acetone, 2-butanone (MEK), tetrahydrofuran, glyme, or a mixture of two or more thereof) can facilitate the reaction. The resulting product can be purified by, for example, distillation. Olefinic reaction by-products (like HFE-Olefins) can be removed (or converted to desired product) by reaction with a reagent that will preferentially react with the olefinic double bond. Such reagents include, for example, anhydrous hydrogen fluoride; potassium bifluoride in a polar, aprotic solvent (with or without a phase transfer catalyst); potassium permanganate in acetone; and elemental bromine with or without irradiation.

In some embodiments, the perfluorinated vinyl amine starting compounds can be prepared by any of a variety of standard synthetic procedures that are well known in the art such as those described in T. Abe, E. Hayashi, H. Baba, H. Fukaya, J. Fluorine Chem. 48 (1990) 257; T. Abe, E. Hayashi, H. Fukaya, H. Baba, J. Fluorine Chem. 50 (1990) 173; T. Abe, E. Hayashi, T. Shimizu, Chem. Lett. 1989, 905; T. Abe, U.S. Pat. No. 4,782,148; and T. Abe, E. Hayashi, Chem. Lett. 1988, 1887.

In some embodiments, representative examples of perfluorinated vinyl amines useful as starting compounds for preparing the nitrogen-containing hydrofluoroether compounds of the present disclosure include:

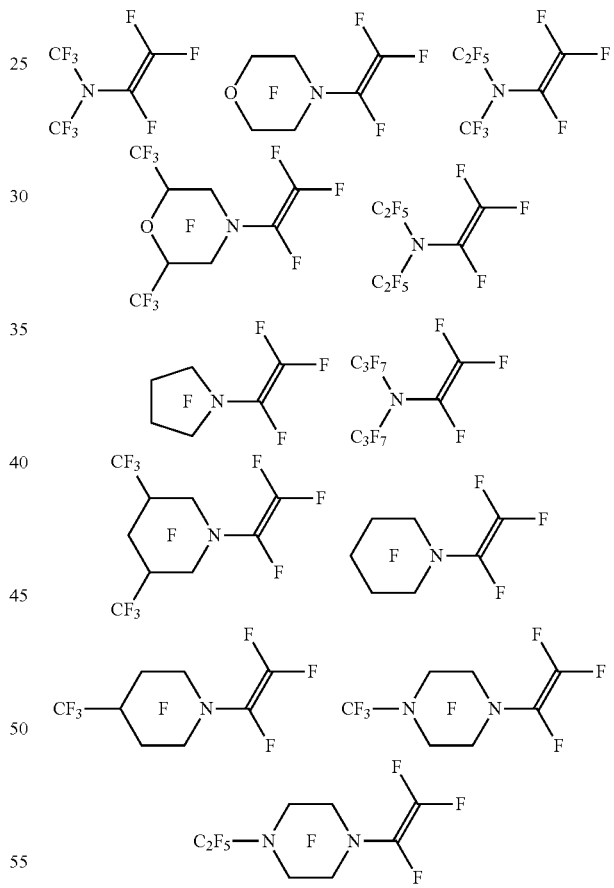

In some embodiments, alcohols that are useful as starting compounds for preparing the nitrogen-containing hydrofluoroether compounds of the present disclosure can be monofunctional or polyfunctional alcohols. In certain embodiments, the alcohols are monofunctional or difunctional. Representative examples of suitable alcohols include methanol, ethanol, isopropanol, 1-propanol, 1-butanol, 2-butanol, 2-methyl-1-propanol, 2-methoxyethanol, allyl alcohol, propargyl alcohol, tetrahydrofurfuryl alcohol, ethylene glycol, 1,4-butanediol, 2-butene-1,4-diol, diethyleneglycol, $(CH_3)_2NC_2H_4OH$, $CF_3CH_2OH$, $C_2F_5CH_2OH$, $C_3F_7CH_2OH$, $(CF_3)_2CHOH$, $HCF_2CF_2CH_2OH$, $H(CF_2CF_2)_2CH_2OH$, $H(CF_2CF_2)_3CH_2OH$, $CF_3CFHCF_2CH_2OH$, $CF_3CFHCF_2CH(CH_3)OH$, $C_4F_9CH_2CH_2OH$, $C_6F_{13}CH_2CH_2OH$, $C_8F_{17}CH_2CH_2OH$, $C_4F_9OCH_2CH_2OH$, $HOCH_2CF_2CF_2CH_2OH$, and the like.

In some embodiments, the alcohols include methanol, ethanol, 1-propanol, 1-butanol, 2-methoxyethanol, allyl alcohol, $(CH_3)_2NC_2H_4OH$, ethylene glycol, 1,4-butanediol, 2-butene-1,4-diol, diethylene glycol, $CF_3CH_2OH$, $HCF_2CF_2CH_2OH$, $H(CF_2CF_2)_2CH_2OH$, $CF_3CFHCF_2CH_2OH$, $CF_3CFHCF_2CH(CH_3)OH$, $C_4F_9CH_2CH_2OH$ and $HOCH_2CF_2CF_2CH_2OH$.

In some embodiments, the present disclosure is further directed to working fluids that include the above-described hydrofluoroether compounds as a major component. For example, the working fluids may include at least 25%, at least 50%, at least 70%, at least 80%, at least 90%, at least 95%, or at least 99% by weight of the above-described hydrofluoroether compounds based on the total weight of the working fluid. In addition to the hydrofluoroether compounds, the working fluids may include a total of up to 75%, up to 50%, up to 30%, up to 20%, up to 10%, or up to 5% by weight of one or more of the following components: alcohols, ethers, alkanes, alkenes, perfluorocarbons, perfluorinated tertiary amines, perfluoroethers, cycloalkanes, esters, ketones, oxiranes, aromatics, siloxanes, hydrochlorocarbons, hydrochlorofluorocarbons, hydrofluorocarbons, hydrofluoroolefins, hydrochlorofluoroolefins, hydrofluoroethers, or mixtures thereof, based on the total weight of the working fluid. Such additional components can be chosen to modify or enhance the properties of a composition for a particular use.

In some embodiments, the present disclosure is further directed to an apparatus for heat transfer that includes a device and a mechanism for transferring heat to or from the device. The mechanism for transferring heat may include a heat transfer working fluid that includes a hydrofluoroether compound of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner.

The provided apparatus may include a mechanism for transferring heat. The mechanism may include a heat transfer fluid. The heat transfer fluid may include one or more hydrofluoroether compounds of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

In some embodiments, the present disclosure is directed to a fire extinguishing composition. The composition may include one or more hydrofluoroether compound of the present disclosure and one or more co-extinguishing agents.

In illustrative embodiments, the co-extinguishing agent may include hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, hydrobromocarbons, iodofluorocarbons, fluorinated ketones, hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, fluorinated ketones, hydrobromocarbons, fluorinated olefins, hydrofluoroolefins, fluorinated sulfones, fluorinated vinylethers, unsaturated fluoro-ethers, bromofluoroolefins, chlorofluorolefins, iodofluoroolefins, fluorinated vinyl amines, fluorinated aminopropenes and mixtures thereof.

Such co-extinguishing agents can be chosen to enhance the extinguishing capabilities or modify the physical properties (e.g., modify the rate of introduction by serving as a propellant) of an extinguishing composition for a particular type (or size or location) of fire and can preferably be utilized in ratios (of co-extinguishing agent to hydrofluoroether compound) such that the resulting composition does not form flammable mixtures in air.

In some embodiments, the hydrofluoroether compounds and the co-extinguishing agent may be present in the fire extinguishing composition in amounts sufficient to suppress or extinguish a fire. The hydrofluoroether compounds and the co-extinguishing agent can be in a weight ratio of from about 9:1 to about 1:9.

In some embodiments, the present disclosure is directed to an apparatus for converting thermal energy into mechanical energy in a Rankine cycle. The apparatus may include a working fluid that includes one or more hydrofluoroether compounds of the present disclosure. The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

In some embodiments, the present disclosure relates to a process for converting thermal energy into mechanical energy in a Rankine cycle. The process may include using a heat source to vaporize a working fluid that includes one or more hydrofluoroether compounds of the present disclosure to form a vaporized working fluid. In some embodiments, the heat is transferred from the heat source to the working fluid in an evaporator or boiler. The vaporized working fluid may pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. In order to prevent methane gas from entering the environment and thus contributing to global warming, the methane gas generated by the landfills can be burned by way of "flares" producing carbon dioxide and water which are both less harmful to the environment in terms of global warming potential than methane. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may expanded though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

The desired thermodynamic characteristics of organic Rankine cycle working fluids are well known to those of ordinary skill and are discussed, for example, in U.S. Pat. Appl. Publ. No. 2010/0139274 (Zyhowski et al.). The greater the difference between the temperature of the heat source and the temperature of the condensed liquid or a provided heat sink after condensation, the higher the Rankine cycle thermodynamic efficiency. The thermodynamic efficiency is influenced by matching the working fluid to the heat source temperature. The closer the evaporating temperature of the working fluid to the source temperature, the higher the efficiency of the system. Toluene can be used, for example, in the temperature range of 79° C. to about 260° C., however toluene has toxicological and flammability concerns. Fluids such as 1,1-dichloro-2,2,2-trifluoroethane and 1,1,1,3,3-pentafluoropropane can be used in this temperature range as an alternative. But 1,1-dichloro-2,2,2-trifluoroethane can form toxic compounds below 300° C. and need to be limited to an evaporating temperature of about 93° C. to about 121° C. Thus, there is a desire for other environmentally-friendly Rankine cycle working fluids with higher critical temperatures so that source temperatures such as gas turbine and internal combustion engine exhaust can be better matched to the working fluid.

The present disclosure relates to the use of the hydrofluoroether compounds of the present disclosure as nucleating agents in the production of polymeric foams and in particular in the production of polyurethane foams and phenolic foams. In this regard, in some embodiments, the present disclosure is directed to a foamable composition that includes one or more blowing agents, one or more foamable polymers or precursor compositions thereof, and one or more nucleating agents that include a hydrofluoroether compound of the present disclosure.

In some embodiments, a variety of blowing agents may be used in the provided foamable compositions including liquid or gaseous blowing agents that are vaporized in order to foam the polymer or gaseous blowing agents that are generated in situ in order to foam the polymer. Illustrative examples of blowing agents include hydrochlorofluorocarbons (HCFCs), hydrofluorocarbons (HFCs), hydrochlorocarbons (HCCs), iodofluorocarbons (IFCs), hydrocarbons, hydrofluoroolefins (HFOs) and hydrofluoroethers (HFEs). The blowing agent for use in the provided foamable compositions can have a boiling point of from about −45° C. to about 100° C. at atmospheric pressure. Typically, at atmospheric pressure the blowing agent has a boiling point of at least about 15° C., more typically between about 20° C. and about 80° C. The blowing agent can have a boiling point of between about 30° C. and about 65° C. Further illustrative examples of blowing agents that can be used in the invention include aliphatic and cycloaliphatic hydrocarbons having about 5 to about 7 carbon atoms, such as n-pentane and cyclopentane, esters such as methyl formate, HFCs such as $CF_3CF_2CHFCHFCF_3$, $CF_3CH_2CF_2H$, $CF_3CH_2CF_2CH_3$, $CF_3CF_2H$, $CH_3CF_2H$ (HFC-152a), $CF_3CH_2CH_2CF_3$ and $CHF_2CF_2CH_2F$, HCFCs such as $CH_3CCl_2F$, $CF_3CHCl_2$, and $CF_2HCl$, HCCs such as 2-chloropropane, and IFCs such as $CF_3I$, and HFEs such as $C_4F_9OCH_3$ and HFOs such as $CF_3CF=CH_2$, $CF_3CH=CHF$, $CF_3CH=CHCl$ and $CF_3CH=CHCF_3$ In certain formulations $CO_2$ generated from the reaction of water with foam precursor such as an isocyanate can be used as a blowing agent.

In various embodiments, the provided foamable composition may also include one or more foamable polymers or a precursor composition thereof. Foamable polymers suitable for use in the provided foamable compositions include, for example, polyolefins, e.g., polystyrene, poly(vinyl chloride), and polyethylene. Foams can be prepared from styrene polymers using conventional extrusion methods. The blowing agent composition can be injected into a heat-plastified styrene polymer stream within an extruder and admixed therewith prior to extrusion to form foam. Representative examples of suitable styrene polymers include, for example, the solid homopolymers of styrene, α-methylstyrene, ring-alkylated styrenes, and ring-halogenated styrenes, as well as copolymers of these monomers with minor amounts of other readily copolymerizable olefinic monomers, e.g., methyl methacrylate, acrylonitrile, maleic anhydride, citraconic anhydride, itaconic anhydride, acrylic acid, N-vinylcarbazole, butadiene, and divinylbenzene. Suitable vinyl chloride polymers include, for example, vinyl chloride homopolymer and copolymers of vinyl chloride with other vinyl monomers. Ethylene homopolymers and copolymers of ethylene with, e.g., 2-butene, acrylic acid, propylene, or butadiene may also be useful. Mixtures of different types of polymers can be employed.

In various embodiments, the foamable compositions of the present disclosure may have a molar ratio of nucleating agent to blowing agent of no more than 1:50, 1:25, 1:9, or 1:7, 1:3, or 1:2.

Other conventional components of foam formulations can, optionally, be present in the foamable compositions of the present disclosure. For example, cross-linking or chain-extending agents, foam-stabilizing agents or surfactants, catalysts and fire-retardants can be utilized. Other possible components include fillers (e.g., carbon black), colorants, fungicides, bactericides, antioxidants, reinforcing agents, antistatic agents, and other additives or processing aids.

In some embodiments, polymeric foams can be prepared by vaporizing at least one liquid or gaseous blowing agent or generating at least one gaseous blowing agent in the presence of at least one foamable polymer or a precursor composition thereof and a nucleating agent as described above. In further embodiments, polymeric foams can be prepared using the provided foamable compositions by vaporizing (e.g., by utilizing the heat of precursor reaction) at least one blowing agent in the presence of a nucleating agent as described above, at least one organic polyisocyanate and at least one compound containing at least two reactive hydrogen atoms. In making a polyisocyanate-based foam, the polyisocyanate, reactive hydrogen-containing compound, and blowing agent composition can generally be combined, thoroughly mixed (using, e.g., any of the various known types of mixing head and spray apparatus), and permitted to expand and cure into a cellular polymer. It is often convenient, but not necessary, to preblend certain of the components of the foamable composition prior to reaction of the polyisocyanate and the reactive hydrogen-containing compound. For example, it is often useful to first blend the reactive hydrogen-containing compound, blowing agent composition, and any other components (e.g., surfactant) except the polyisocyanate, and to then combine the resulting mixture with the polyisocyanate. Alternatively, all components of the foamable composition can be introduced separately. It is also possible to pre-react all or a portion of the reactive hydrogen-containing compound with the polyisocyanate to form a prepolymer.

In some embodiments, the present disclosure is directed to dielectric fluids that include one or more hydrofluoroether compounds of the present disclosure, as well as to electrical devices (e.g., capacitors, switchgear, transformers, or electric cables or buses) that include such dielectric fluids. For purposes of the present application, the term "dielectric fluid" is inclusive of both liquid dielectrics and gaseous dielectrics. The physical state of the fluid, gaseous or liquid, is determined at the operating conditions of temperature and pressure of the electrical device in which it is used.

In some embodiments, the dielectric fluids include one or more hydrofluoroether compounds of the present disclosure and, optionally, one or more second dielectric fluids. Suitable second dielectric fluids include, for example, air, nitrogen, helium, argon, and carbon dioxide, or combinations thereof. The second dielectric fluid may be a non-condensable gas or an inert gas. Generally, the second dielectric fluid may be used in amounts such that vapor pressure is at least 70 kPa at 25° C., or at the operating temperature of the electrical device.

The dielectric fluids of the present application are useful for electrical insulation and for arc quenching and current interruption equipment used in the transmission and distribution of electrical energy. Generally, there are three major types of electrical devices in which the fluids of the present disclosure can be used: (1) gas-insulated circuit breakers and current-interruption equipment, (2) gas-insulated transmission lines, and (3) gas-insulated transformers. Such gas-insulated equipment is a major component of power transmission and distribution systems.

In some embodiments, the present disclosure provides electrical devices, such as capacitors, comprising metal electrodes spaced from each other such that the gaseous dielectric fills the space between the electrodes. The interior space of the electrical device may also comprise a reservoir of the liquid dielectric fluid which is in equilibrium with the gaseous dielectric fluid. Thus, the reservoir may replenish any losses of the dielectric fluid.

In some embodiments, the present disclosure relates to coating compositions that include a solvent composition that one or more hydrofluoroether compounds of the present disclosure, and one or more coating materials which are soluble or dispersible in the solvent composition.

In various embodiments, the coating materials of the coating compositions may include pigments, lubricants, stabilizers, adhesives, anti-oxidants, dyes, polymers, pharmaceuticals, release agents, inorganic oxides, and the like, and combinations thereof. For example, coating materials may include perfluoropolyether, hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, perfluoropolyethers, polysiloxanes, stearic acid, acrylic adhesives, polytetrafluoroethylene, amorphous copolymers of tetrafluoroethylene, or combinations thereof.

In some embodiments, the above-described coating compositions can be useful in coating deposition, where the hydrofluoroether compound function as a carrier for a coating material to enable deposition of the material on the surface of a substrate. In this regard, the present disclosure further relates to a process for depositing a coating on a substrate surface using the coating composition. The process comprises the step of applying to at least a portion of at least one surface of a substrate a coating of a liquid coating composition comprising (a) a solvent composition containing one or more hydrofluoroether compounds of the present disclosure; and (b) one or more coating materials which are soluble or dispersible in the solvent composition. The solvent composition can further comprise one or more co-dispersants or co-solvents and/or one or more additives (e.g., surfactants, coloring agents, stabilizers, anti-oxidants, flame retardants, and the like). Preferably, the process further comprises the step of removing the solvent composition from the coating by, e.g., allowing evaporation (which can be aided by the application of, e.g., heat or vacuum).

In various embodiments, to form a coating composition, the components of the coating composition (i.e., the hydrofluoroether compound(s), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating. For example, the coating material(s) may constitute from about 0.1 to about 10 weight percent of the coating composition.

In illustrative embodiments, the deposition process of the disclosure can be carried out by applying the coating composition to a substrate by any conventional technique. For example, the composition can be brushed or sprayed (e.g., as an aerosol) onto the substrate, or the substrate can be spin-coated. In some embodiments, the substrate may be coated by immersion in the composition. Immersion can be carried out at any suitable temperature and can be maintained for any convenient length of time. If the substrate is a tubing, such as a catheter, and it is desired to ensure that the composition coats the lumen wall, the composition may be drawn into the lumen by the application of reduced pressure.

In various embodiments, after a coating is applied to a substrate, the solvent composition can be removed from the coating (e.g., by evaporation). If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Both organic and inorganic substrates can be coated by the processes of the present disclosure. Representative examples of the substrates include metals, ceramics, glass, polycarbonate, polystyrene, acrylonitrile-butadiene-styrene copolymer, natural fibers (and fabrics derived therefrom) such as cotton, silk, fur, suede, leather, linen, and wool, synthetic fibers (and fabrics) such as polyester, rayon, acrylics, nylon, or blends thereof, fabrics including a blend of natural and synthetic fibers, and composites of the foregoing materials. In some embodiments, substrates that may be coated include, for example, magnetic hard disks or electrical connectors with perfluoropolyether lubricants or medical devices with silicone lubricants.

In some embodiments, the present disclosure relates to cleaning compositions that include one or more hydrofluoroether compounds of the present disclosure, and one or more co-solvents.

In some embodiments, the hydrofluoroether compounds may be present in an amount greater than 50 weight percent, greater than 60 weight percent, greater than 70 weight percent, or greater than 80 weight percent based upon the total weight of the hydrofluoroether compounds and the co-solvent(s).

In various embodiments, the cleaning composition may further comprise a surfactant. Suitable surfactants include those surfactants that are sufficiently soluble in the fluorinated olefin, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylatedalkyl phenols, ethoxylated fatty acids, alkylarysulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble oil removal. The surfactant, if used, can be added in an amount sufficient to promote soil removal. Typically, surfactant is added in amounts from about 0.1 to 5.0 wt. %, preferably in amounts from about 0.2 to 2.0 wt. % of the cleaning composition.

In illustrative embodiments, the co-solvent may include alcohols, ethers, alkanes, alkenes, haloalkenes, perfluorocarbons, perfluorinated tertiary amines, perfluoroethers, cycloalkanes, esters, ketones, aromatics, haloaromatics, siloxanes, hydrochlorocarbons, hydrochlorofluorocarbons, hydrochlorofluoroolefins, hydrofluorocarbons, or mixtures thereof. Representative examples of co-solvents which can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof.

In some embodiments, the present disclosure relates to a process for cleaning a substrate. The cleaning process can be carried out by contacting a contaminated substrate with a cleaning composition as discussed above. The hydrofluoroether compounds can be utilized alone or in admixture with each other or with other commonly-used cleaning solvents, e.g., alcohols, ethers, alkanes, alkenes, perfluorocarbons, perfluorinated tertiary amines, perfluoroethers, cycloalkanes, esters, ketones, aromatics, siloxanes, hydrochlorocarbons, hydrochlorofluorocarbons, hydrochlorofluoroolefins, hydrofluoroolefins, hydrofluorocarbons, or mixtures thereof. Such co-solvents can be chosen to modify or enhance the solvency properties of a cleaning composition for a particular use and can be utilized in ratios (of co-solvent to hydrofluoroether compounds) such that the resulting composition has no flash point. If desirable for a particular application, the cleaning composition can further contain one or more dissolved or dispersed gaseous, liquid, or solid additives (for example, carbon dioxide gas, surfactants, stabilizers, antioxidants, or activated carbon).

In some embodiments, the present disclosure relates to cleaning compositions that include one or more hydrofluoroether compounds of the present disclosure and optionally one or more surfactants. Suitable surfactants include those surfactants that are sufficiently soluble in the hydrofluoroether compounds, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylated alkylphenols, ethoxylated fatty acids, alkylaryl sulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble soil removal. The surfactant, if used, can be added in an amount sufficient to promote soil removal. Typically, surfactant may be added in amounts from 0.1 to 5.0 wt. % or from 0.2 to 2.0 wt. % of the cleaning composition.

The cleaning processes of the disclosure can also be used to dissolve or remove most contaminants from the surface of a substrate. For example, materials such as light hydrocarbon contaminants; higher molecular weight hydrocarbon contaminants such as mineral oils and greases; fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes; particulates; water; and other contaminants encountered in precision, electronic, metal, and medical device cleaning can be removed.

The cleaning compositions can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in Cleaning and Contamination of Electronics Components and Assemblies, Electrochemical Publications Limited, Ayr, Scotland, pages 182-94 (1986).

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

In some embodiments, the present disclosure further relates to electrolyte compositions that include one or more hydrofluoroether compounds of the present disclosure. The electrolyte compositions may comprise (a) a solvent composition including one or more of the hydrofluoroether compounds; and (b) at least one electrolyte salt. The electrolyte compositions of the present disclosure exhibit excellent oxidative stability, and when used in high voltage electrochemical cells (such as rechargeable lithium ion batteries) provide outstanding cycle life and calendar life. For example, when such electrolyte compositions are used in an electrochemical cell with a graphitized carbon electrode, the electrolytes provide stable cycling to a maximum charge voltage of at least 4.5V and up to 6.0V vs. $Li/Li^+$.

Electrolyte salts that are suitable for use in preparing the electrolyte compositions of the present disclosure include those salts that comprise at least one cation and at least one weakly coordinating anion (the conjugate acid of the anion having an acidity greater than or equal to that of a hydrocarbon sulfonic acid (for example, a bis(perfluoroalkanesulfonyl)imide anion); that are at least partially soluble in a selected hydrofluoroether compound (or in a blend thereof with one or more other hydrofluoroether compounds or one or more conventional electrolyte solvents); and that at least partially dissociate to form a conductive electrolyte composition. The salts may be stable over a range of operating voltages, are non-corrosive, and are thermally and hydrolytically stable. Suitable cations include alkali metal, alkaline earth metal, Group JIB metal, Group IIIB metal, transition metal, rare earth metal, and ammonium (for example, tetraalkylammonium or trialkylammonium) cations, as well as a proton. In some embodiments, cations for battery use include alkali metal and alkaline earth metal cations. Suitable anions include fluorine-containing inorganic anions such as $(FSO_2)_2N^-$, $BF_4^-$, $PF_6^-$, $AsF_6^-$, and $SbF_6^-$; $ClO_4^-$; $HSO_4^-$; $H_2PO_4^-$; organic anions such as alkane, aryl, and alkaryl sulfonates; fluorine-containing and nonfluorinated tetraarylborates; carboranes and halogen-, alkyl-, or haloalkylsubstituted carborane anions including metallocarborane anions; and fluorine-containing organic anions such as perfluoroalkanesulfonates, cyanoperfluoroalkanesulfonylamides, bis(cyano)perfluoroalkanesulfonylmethides, bis(perfluoroalkanesulfonyl)imides, bis(perfluoroalkanesulfonyl)methides, and tris(perfluoroalkanesulfonyl)methides; and the like. Preferred anions for battery use include fluorine-containing inorganic anions (for example, $(FSO_2)_2N^-$, $BF_4^-$, $PF_6^-$, and $AsF_6^-$) and fluorine-containing organic anions (for example, perfluoroalkanesulfonates, bis(perfluoroalkanesulfonyl)imides, and tris(perfluoroalkanesulfonyl)methides). The fluorine-containing organic anions can be either fully fluorinated, that is perfluorinated, or partially fluorinated (within the organic portion thereof). In some embodiments, the fluorine-containing organic anion is at least about 80 percent fluorinated (that is, at least about 80 percent of the carbon-bonded substituents of the anion are fluorine atoms). In some embodiments, the anion is perfluorinated (that is, fully fluorinated, where all of the carbon-bonded substituents are fluorine atoms). The anions, including the perfluorinated anions, can contain one or more catenary heteroatoms such as, for example, nitrogen, oxygen, or sulfur. In some embodiments, fluorine-containing organic anions include perfluoroalkanesulfonates, bis(perfluoroalkanesulfonyl)imides, and tris(perfluoroalkanesulfonyl)methides.

In some embodiments, the electrolyte salts may include lithium salts. Suitable lithium salts include, for example, lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis(fluorosulfonyl)imide (Li—FSI), and mixtures of two or more thereof.

The electrolyte compositions of the present disclosure can be prepared by combining at least one electrolyte salt and a solvent composition including at least one hydrofluoroether compound of the present disclosure, such that the salt is at least partially dissolved in the solvent composition at the desired operating temperature. The hydrofluoroether compounds (or a normally liquid composition including, consisting, or consisting essentially thereof) can be used in such preparation.

In some embodiments, the electrolyte salt is employed in the electrolyte composition at a concentration such that the conductivity of the electrolyte composition is at or near its maximum value (typically, for example, at a Li molar concentration of around 0.1-4.0 M, or 1.0-2.0 M, for electrolytes for lithium batteries), although a wide range of other concentrations may also be employed.

In some embodiments, one or more conventional electrolyte solvents are mixed with the hydrofluoroether compound(s) (for example, such that the hydrofluoroether(s) constitute from about 1 to about 80 or 90 percent of the resulting solvent composition). Useful conventional electrolyte solvents include, for example, organic and fluorine-containing electrolyte solvents (for example, propylene carbonate, ethylene carbonate, dimethyl carbonate, diethyl carbonate, ethyl methyl carbonate, dimethoxyethane, 7-butyrolactone, diglyme (that is, diethylene glycol dimethyl ether), tetraglyme (that is, tetraethylene glycol dimethyl ether), monofluoroethylene carbonate, vinylene carbonate, ethyl acetate, methyl butyrate, tetrahydrofuran, alkyl-substituted tetrahydrofuran, 1, 3-dioxolane, alkyl-substituted 1, 3-dioxolane, tetrahydropyran, alkyl-substituted tetrahydropyran, and the like, and mixtures thereof). Other conventional electrolyte additives (for example, a surfactant) can also be present, if desired.

The present disclosure further relates to electrochemical cells (e.g., fuel cells, batteries, capacitors, electrochromic windows) that include the above-described electrolyte compositions. Such an electrochemical cell may include a positive electrode, a negative electrode, a separator, and the above-described electrolyte composition.

An electrochemical device using the electrolyte compositions described herein may, in some embodiments, have a discharge capacity of greater than 50%, preferably greater than 80% of theoretical, at a discharge current of up to 12 C. An electrochemical cell including the electrolyte composition described in this disclosure may, in some embodiments, have a charge capacity of greater than about 40%, preferably greater than about 60% of theoretical, at a charge current of up to 6 C. An electrochemical cell including the electrolyte compositions described herein may, in some embodiments, have excellent low temperature performance, and may retain over 90% of its discharge capacity at 25° C. when exposed to ambient temperatures from 0° C. to −20° C. The electrochemical cell including the presently described electrolyte compositions may, in some embodiments, retain a discharge capacity of greater than 150 mAh per gram of cathode over up to 30 charging cycles at up to 4.5V.

A variety of negative and positive electrodes may be employed in the electrochemical cells. Representative negative electrodes include graphitic carbons e. g., those having a spacing between (002) crystallographic planes, $d_{002}$, of 3.45 A>$d_{002}$>3.354 A and existing in forms such as powders, flakes, fibers or spheres (e. g., mesocarbon microbeads); $Li_{4/3}Ti_{5/3}O_4$ the lithium alloy compositions described in U.S. Pat. No. 6,203,944 (Turner '944) entitled "ELECTRODE FOR A LITHIUM BATTERY" and PCT Published Patent Application No. WO 00103444 (Turner PCT) entitled "ELECTRODE MATERIAL AND COMPOSITIONS"; and combinations thereof. Representative positive electrodes include $LiFePO_4$, $LiMnPO_4$, $LiCoPO_4$, $LiMn_2O_4$, $LiCoO_2$ and combinations thereof. The negative or positive electrode may contain additives such as will be familiar to those skilled in the art, e. g., carbon black for negative electrodes and carbon black, flake graphite and the like for positive electrodes.

The electrochemical devices of the invention can be used in various electronic articles such as computers, power tools, automobiles, telecommunication devices, and the like.

Embodiments

1. A hydrofluoroether compound represented by the following general formula (1):

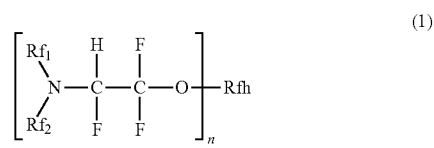

wherein n is 1-2, and each occurrence of $Rf_1$ and $Rf_2$ is:
(i) independently a linear or branched perfluoroalkyl group having 1-8 carbon and optionally comprises one or more catenated heteroatoms; or
(ii) bonded together to form a ring structure having 4-8 carbon atoms and optionally comprises one or more catenated heteroatoms; and Rfh is, when n=1, a substituted or unsubstituted, monovalent, hydrocarbon group having 1-12 carbon atoms optionally comprising one or more catenary heteroatoms and, when n=2, a substituted or unsubstituted, divalent, hydrocarbon group having 1-12 carbon atoms optionally comprising one or more catenary heteroatoms.

2. The hydrofluoroether compound according to embodiment 1, wherein each occurrence of $Rf_1$ and $Rf_2$ is:
(i) independently a linear or branched perfluoralkyl group having 1-4 carbons and optionally comprises one or more catenated heteroatoms; or (ii) bonded together to form a ring structure having 4-6 or carbon atoms and optionally comprises one or more catenated heteroatoms.

3. The hydrofluoroether compound according to any one of the previous embodiments, wherein Rfh is substituted with halogen atoms.

4. The hydrofluoroether compound according to any one of the previous embodiments, wherein Rfh is substituted with fluorine atoms.

5. The hydrofluoroether compound according to any one of the previous embodiments, wherein the hydrofluoroether compound has a degree of fluorination that is at least 60%.

7. A fire extinguishing composition comprising:
(a) a hydrofluoroether compound according to any one of embodiments 1-5;
(b) at least one co-extinguishing agent comprising one or more hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, fluorinated ketones, hydrobromocarbons, fluorinated olefins, hydrofluoroolefins, fluorinated sulfones, fluorinated vinylethers, and mixtures thereof,
wherein (a) and (b) are present in an amount sufficient to suppress or extinguish a fire.

8. A fire extinguishing composition according to embodiment 7, wherein (a) and (b) are in a weight ratio of from about 9:1 to about 1:9.

9. A method of extinguishing a fire comprising:
 applying to the fire a fire extinguishing composition comprising a hydrofluoroether compound according to any one of embodiments 1-5; and
 suppressing the fire.

10. A method of extinguishing a fire according to embodiment 9, wherein the fire extinguishing composition further comprises at least one co-extinguishing agent comprising one or more hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, fluorinated ketones, hydrobromocarbons, fluorinated olefins, hydrofluoroolefins, fluorinated sulfones, fluorinated vinylethers, and mixtures thereof.

11. An apparatus for converting thermal energy into mechanical energy in a Rankine cycle comprising:
 a working fluid;
 a heat source to vaporize the working fluid and form a vaporized working fluid;
 a turbine through which the vaporized working fluid is passed thereby converting thermal energy into mechanical energy;
 a condenser to cool the vaporized working fluid after it is passed through the turbine; and
 a pump to recirculate the working fluid,
 wherein the working fluid comprises a hydrofluoroether compound according to any one of embodiments 1-5.

12. A process for converting thermal energy into mechanical energy in a Rankine cycle comprising:
 vaporizing a working fluid with a heat source to form a vaporized working fluid;
 expanding the vaporized working fluid through a turbine;
 cooling the vaporized working fluid using a cooling source to form a condensed working fluid; and
 pumping the condensed working fluid;
 wherein the working fluid comprises a hydrofluoroether compound according to any one of embodiments 1-5.

13. A process for recovering waste heat comprising:
 passing a liquid working fluid through a heat exchanger in communication with a process that produces waste heat to produce a vaporized working fluid;
 removing the vaporized working fluid from the heat exchanger;
 passing the vaporized working fluid through an expander, wherein the waste heat is converted into mechanical energy; and
 cooling the vaporized working fluid after it has been passed through the expander;
 wherein the working fluid comprises a hydrofluoroether compound according to any one of embodiments 1-5.

14. A foamable composition comprising:
 a blowing agent;
 a foamable polymer or a precursor composition thereof; and
 a nucleating agent, wherein said nucleating agent comprises a hydrofluoroether compound according to any one of embodiments 1-5.

15. A foamable composition according to embodiment 14, wherein the nucleating agent and the blowing agent are in a molar ratio of less than 1:2.

16. A foamable composition according to any one of embodiments 14-15, wherein the blowing agent comprises an aliphatic hydrocarbon having from about 5 to about 7 carbon atoms, a cycloaliphatic hydrocarbon having from about 5 to about 7 carbon atoms, a hydrocarbon ester, water, or combinations thereof.

17. A process for preparing polymeric foam comprising:
 vaporizing at least one liquid or gaseous blowing agent or generating at least one gaseous blowing agent in the presence of at least one foamable polymer or a precursor composition thereof and a nucleating agent, wherein said nucleating agent comprises a hydrofluoroether compounding according to any one of embodiments 1-5.

18. A foam made with the foamable composition according to any one of embodiments 14-16.

19. A device comprising:
 a dielectric fluid comprising a hydrofluoroether compound according to any one of embodiments 1-5;
 wherein the device is an electrical device.

20. The device of embodiment 15, wherein said electrical device comprises a gas-insulated circuit breakers, current-interruption equipment, a gas-insulated transmission line, a gas-insulated transformers, or a gas-insulated substation.

21. The device according to any one of embodiments 19-20, wherein the dielectric fluid further comprises a second dielectric gas.

22. The device of embodiment 21, wherein the second dielectric gas comprises an inert gas.

23. The device of embodiment 22, wherein the second dielectric gas comprises nitrogen, helium, argon, or carbon dioxide.

24. A coating composition comprising:
 a solvent composition comprising a hydrofluoroether compound according to any one of embodiments 1-5; and
 a coating material that is soluble or dispersible in said solvent composition.

25. The coating composition according to embodiment 24, wherein said coating material comprises a pigment, lubricant, stabilizer, adhesive, anti-oxidant, dye, polymer, pharmaceutical, release agent, inorganic oxide.

26. The composition according to embodiment 24, wherein said coating material comprises a perfluoropolyether, a hydrocarbon, a silicone lubricant, a copolymer of tetrafluoroethylene, or a polytetrafluoroethylene.

27. A cleaning composition comprising:
 a hydrofluoroether compound according to any one of embodiments 1-5; and
 a co-solvent.

28. The composition of embodiment 27, wherein said hydrofluoroether compound is greater than 50 percent by weight of said composition based on the total weights of the fluorinated compound and the co-solvent.

29. The composition according to any one of embodiments 27-28, wherein said co-solvent comprises alcohols, ethers, alkanes, alkenes, haloalkenes, perfluorocarbons, perfluorinated tertiary amines, perfluoroethers, cycloalkanes, esters, ketones, aromatics, haloaromatics, siloxanes, hydrochlorocarbons, hydrochlorofluorocarbons, hydrochlorofluoroolefins, hydrofluoroolefins, hydrofluorocarbons, or mixtures thereof.

30. A cleaning composition comprising:
 a hydrofluoroether compound according to any one of embodiments 1-5; and
 a surfactant.

31. The cleaning composition of embodiment 30, wherein the cleaning composition comprises from 0.1 to 5 percent by weight surfactant.

32. The composition according to any one of embodiments 30-31, wherein the surfactant comprises a nonionic surfactant comprising an ethoxylated alcohol, an ethoxylated alkylphenol, an ethoxylated fatty acid, an alkylaryl sulfonate, a glycerolester, an ethoxylated fluoroalcohol, a fluorinated sulfonamide, or mixtures thereof.

33. A process for removing contaminants from a substrate, the process comprising the steps of:
  contacting a substrate with a composition comprising:
    a hydrofluoroether compound according to any one of embodiments 1-5; and
    a co-solvent.
34. An electrolyte composition comprising:
  a solvent composition comprising at least one hydrofluoroether compound according to any one of embodiments 1-5; and
  an electrolyte salt.

The operation of the present disclosure will be further described with regard to the following detailed examples. These examples are offered to further illustrate various embodiments and techniques. It should be understood, however, that many variations and modifications may be made while remaining within the scope of the present disclosure.

EXAMPLES

Example 1: Synthesis of $O(CF_2CF_2)_2NCFHCF_2OCH_3$, 2,2,3,3,5,5,6,6-octafluoro-4-(1,2,2-trifluoro-2-methoxy-ethyl)morpholine

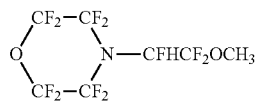

Perfluoro-vinylmorpholine (200.00 g, 0.6430 mol) and anhydrous methanol (200.00 g, 6.242 mol) were charged to a 1.0 L 3-necked round bottomed flask equipped with a magnetic stir bar, water cooled condenser, nitrogen inlet line, and a 60 mL addition funnel. A 5.0 Molar solution of sodium methoxide in methanol (40.0 g, 0.2147 mol) was charged to the addition funnel and added dropwise over a one hour period with stirring to the reaction mixture starting at 21° C. A slightly exothermic reaction ensued, causing the reaction mixture to reach a maximum temperature of 52° C. with no external cooling. After a reaction time of 3 hours at 21-52° C., the reaction appeared to be complete judging from the disappearance of the lower perfluoro-vinylmorpholine liquid phase, but the reaction was allowed to continue with stirring at room temperature for another three days. Analysis of the reaction mixture by GC-FID and GC-MS revealed 100% conversion of the perfluoro-vinylmorpholine to 87% desired HFE-Hydride, $O(CF_2CF_2)_2NCFHCF_2OCH_3$, and 9% of the corresponding HFE-Olefin, $O(CF_2CF_2)_2NCF=CFOCH_3$ (cis and trans mixture). This reaction mixture was quenched with 500 mL of water at room temperature with stirring producing two non-miscible liquid phases. The pH of the reaction mixture was adjusted to approximately neutral (pH 5) by addition of 2.3 grams of 34.4% $H_3PO_{4(aq)}$ and the reaction mixture was transferred to a 1.0 L separatory funnel. The lower fluorochemical phase was isolated and then washed with three 400 mL portions of deionized water. After the final water wash the isolated lower fluorochemical phase (193.8 g) was transferred to a dry Erlenmeyer flask and dried over 3 A molecular sieves. The dried fluorochemical phase was then transferred to 250 mL, 3-necked round bottomed flask equipped with a 40-plate concentric tube distillation column and distillation head and purified by fractional distillation under a nitrogen atmosphere at atmospheric pressure. The main product cuts (158.5 g) were collected at 125.7-127.7° C. (head temperature) and consisted of about 96% desired HFE-Hydride, $O(CF_2CF_2)_2NCFHCF_2OCH_3$, the remainder comprising mainly the HFE-Olefin byproduct, $O(CF_2CF_2)_2NCF=CFOCH_3$ (cis and trans mixture) by GC.

An approximately 95:5 mixture of $O(CF_2CF_2)_2NCFHCF_2OCH_3$ and $O(CF_2CF_2)_2NCF=CFOCH_3$ prepared as described above (213.5 g, 0.622 mol) was transferred to a 250 mL HDPE polybottle equipped with magnetic stirring bar and treated neat (no solvent) with anhydrous hydrogen fluoride (13.0 g, 0.65 mol) with stirring at room temperature. This mixture was allowed to stir for 3 days at room temperature in the loosely capped polybottle followed by quenching (dropwise initially to control exotherm) with deionized water (88.0 g). The resulting two-phase mixture was transferred to a Teflon separatory funnel and the lower fluorochemical phase was isolated and then washed with three 128 mL portions of deionized water to remove residual HF. After the final water wash, the lower fluorochemical product phase (209.1 g) was drained to a dry Erlenmeyer flask and dried over 3 A molecular sieves. After drying overnight, the fluorochemical product was analyzed by GC-FID, revealing that HF addition to the HFE-Olefin byproduct, $O(CF_2CF_2)_2NCF=CFOCH_3$, was complete and the product was 98.7% pure HFE-Hydride, $O(CF_2CF_2)_2NCFHCF_2OCH_3$. No residual HFE-Olefin byproduct was detected. This material was then fractionally distilled as before to remove other impurities. The main product distillation cuts (Fractions 3, 4 and 5, 190.10 g total) distilled at 127.0-127.3° C. and had a GC purity of >99%. GC peak assignments were confirmed by GC-MS and the purity of combined cuts 4 and 5 (120.6 g) determined by quantitative $^1H$ and $^{19}F$ NMR spectroscopy was 99.3% by wt overall (sum of three desired product isomers, absolute wt %), including 99.1 wt % $O(CF_2CF_2)_2NCFHCF_2OCH_3$ plus two minor isomers. The purified $O(CF_2CF_2)_2NCFHCF_2OCH_3$ product was a non-viscous liquid at room temperature and was determined to be non-flammable (no closed cup flash point up to 200° F.). It had a measured density of 1.64 g/mL, a specific heat capacity (measured by DSC at room temperature) of 0.25 calories/gram° C. and an estimated Log KOW (oil/water partition coefficient measured by HPLC) of 4.46. The 4 hour LC-50 and the NOAEL (No Observable Adverse Effect Level) in male Sprague-Dawley rats were both determined to be >5000 ppm (v/v), based on acute inhalation toxicity testing in animals dosed at 5000 ppm for 4 hours. All animals survived and appeared normal during 14 day post dose recovery period. Aside from slightly increased respiration rates during 4 hour dosing, no significant clinical observations or body or organ weight effects were noted.

Example 2: Synthesis of $O(CF_2CF_2)_2NCFHCF_2OCH_2CF_2CF_2H$, 2,2,3,3,5,5,6,6-octafluoro-4-[1,2,2-trifluoro-2-(2,2,3,3-tetrafluoropropoxy)ethyl]morpholine

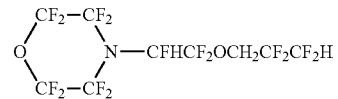

The reagents 2,2,3,3,5,5,6,6-octafluoro-4-(1,2,2-trifluorovinyl)morpholine (179.11 g, 98.9% pure by GC), 2,2,3,3-tetrafluoropropanol (80.687 g, TCI America, 98.0%), and 543 mL of acetonitrile (Aldrich, Anyhydrous) were combined in a 3-necked, 1000 mL round bottom flask equipped with magnetic stirring, a Teflon coated thermocouple probe, and a water-cooled condenser with $N_2$ inlet. The reaction mixture was initially biphasic. Then potassium carbonate (8.445 g, 325 mesh, Armand Product Co) was added batchwise to the reaction mixture at room temperature with stirring. A wet ice bath was placed around reaction vessel to control the reaction exotherm and keep the reaction temperature near 25° C. After stirring for 2 hours the reaction mixture was analyzed by GC-FID and the reaction was found to be 95.3% complete. After 4 hours an additional 0.075 g of powdered potassium carbonate was charged to the reaction mixture and stirred for an additional 30 minutes prior to GC-FID analysis, which indicated that the reaction was greater than 99.5% complete. Once the reaction was essentially complete, the reaction mixture was filtered through a sintered glass fritted funnel by suction to remove insoluble solids. The filtered reaction mix was transferred to a 1000 mL round bottomed flask and acetonitrile solvent was removed by fractional distillation. After nearly all the acetonitrile (and residual $HCF_2CF_2CH_2OH$) was removed, the yield of crude product remaining in the pot was 197.01 g. GC-FID analysis of the pot retains indicates that the crude product comprises 80.98% desired HFE-Hydride, $O(CF_2CF_2)_2NCFHCF_2OCH_2CF_2CF_2H$, and 17.0% HFE-Olefin byproduct, $O(CF_2CF_2)_2NCF=CFOCH_2CF_2CF_2H$ (cis and trans isomers). The crude fluorochemical product mixture was transferred to a 250 mL HDPE polybottle equipped with a magnetic stir bar and treated with excess anhydrous HF (~90 grams). The polybottle was loosely capped and the mixture stirred magnetically at room temperature for 72 hours. The remaining anhydrous HF was then quenched and diluted with 90 mL water (added dropwise initially, to control exotherm). The resulting two-phase liquid mixture was transferred to a Teflon reparatory funnel and the lower fluorochemical product phase (196.9 g) was separated from the upper aqueous HF phase. The fluorochemical phase was then washed with three 100 mL portions of water to remove residual HF from the product phase. The pH of the final water wash was 7.0 and the yield of crude fluorochemical product after washing was 191.5 g. GC-FID analysis of this material indicates that the HF treatment has reduced the level of HFE-Olefin byproducts (cis and trans isomers) to only 0.76%, the balance being mostly (97.89%) desired HFE-Hydride. This material was transferred to an HDPE poly bottle and stored over 3 A molecular sieves to dry. After storing over molecular sieves for a minimum of 48 hours the crude fluorochemical product was purified by fractional distillation under nitrogen at atmospheric pressure using a 40-plate concentric tube distillation column and a distillation head equipped with a water-cooled condenser and liquid splitter. The main product distillation cuts (Fractions 8-12) were collected at 164.2-164.9° C. (head temperature) and consisted of >98% pure HFE-Hydride, $O(CF_2CF_2)_2NCFHCF_2OCH_2CF_2CF_2H$. The highest purity distillation cut (Fraction 10) was analyzed by GC-MS, which confirmed that the desired HFE-Hydride product was present in ~99% purity. Quantitative analysis of this material by $^1H$ and $^{19}F$ NMR spectroscopy showed that the final product contained 99.17% (absolute wt %) of the desired HFE-Hydride, $O(CF_2CF_2)_2NCFHCF_2OCH_2CF_2CF_2H$.

The acute single dose oral toxicity of $O(CF_2CF_2)_2NCFHCF_2OCH_2CF_2CF_2H$ was examined in rats dosed at 300 mg/kg body weight. No adverse clinical observations were noted during the post dose recovery period and necropsy results were normal for all animals. Based on this study, the $LD_{50}$ of 2,2,3,3,5,5,6,6-octafluoro-4-[1,2,2-trifluoro-2-(2,2,3,3-tetrafluoropropoxy)ethyl]morpholine is estimated to be >300 mg/kg body weight.

Example 3: Synthesis of $O(CF_2CF_2)_2NCFHCF_2OCH_2CH_2OCH_3$, 2,2,3,3,5,5,6,6-octafluoro-4-[1,2,2-trifluoro-2-(2-methoxy)ethyl]morpholine

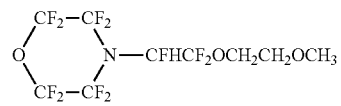

The reagents 2,2,3,3,5,5,6,6-octafluoro-4-(1,2,2-trifluoro-vinyl)morpholine (200.00 g, >98.9%), acetonitrile (236 g, Aldrich Anhydrous, 99.8%), potassium hydroxide (3.608 g, powdered, Fluka, >85%) and sodium bromide (6.616 g, granular, EMD, 99%) were combined in a 3-neck 1000 mL round bottom flask equipped with overhead stirring, a water cooled condenser with $N_2$ inlet, a Claisen adapter with Teflon coated thermocouple probe and an addition funnel. While the reaction mixture was stirring, 2-methoxy-ethanol (76.09 g, TCI America, 98%) was charged to the reaction mixture over 3 hours. A slightly exothermic reaction was observed causing the reaction temperature to rise to 26° C. The reaction was stirred for 2 hours following addition of all the alcohol before a sample was removed by pipette, filtered through a PVDF filter disc and analyzed by GC-FID. GC analysis indicated that the desired reaction had proceeded to 93% conversion. The reaction mixture was stirred for an additional 4 hours and then quenched with 400 mL deionized water and 100 g of concentrated sodium chloride brine solution. The fluorochemical product separated from aqueous solution forming a lower liquid phase. The fluorochemical phase was isolated and washed with three additional 200 mL portions of water to remove residual acetonitrile and then dried over molecular sieves for a minimum of three days. After drying, the crude fluorochemical product was treated with 30 g anhydrous hydrofluoric acid to remove the minor olefinic byproducts, 4-[(E&Z)-1,2-difluoro-2-(2-methoxyethoxy)vinyl]-2,2,3,3,5,5,6,6-octafluoro-morpholine, and convert them to the desired HF addition product. The HF treatment was allowed to proceed overnight at room temperature with magnetic stirring in a well ventilated and scrubbed fume hood. The following morning, residual HF was removed by quenching with 125 mL of water (adding the water dropwise initially to control exotherm), isolating the lower fluorochemical product phase and then washing with three 125 mL portions of water to remove residual HF (pH of final aqueous wash was 6.5). Once isolated, the crude fluorochemical product was dried again over molecular sieves for a minimum of three days and then purified by fractional distillation through a concentric tube distillation column giving 76.46 g of product distillate (B.P.=177-178° C.) as a clear colorless liquid with an average purity of 99.41% by GC-FID. The identity of the product was confirmed by GC/MS and the chemical structure and purity was verified by quantitative $^{19}F$ and $^1H$ NMR spectroscopy showing that the distillate consisted of 99 wt % 2,2,3,3,5,5,6,6-octafluoro-4-[1,2,2-trifluoro-2-(2-methoxy)ethyl]morpholine.

Examples 4-30: Vial Reactions of Perfluorinated Vinyl Amines with Various Alcohols The following examples were prepared by the following general method:
$K_2CO_3$ powder, anhydrous $CH_3CN$, perfluoro-vinylamine and the alcohol reagent were charged to a 7 mL glass vial in the order indicated (in air). A mini stir bar was added and the vial was then tightly capped and rapid stirring initiated at the temperature indicated in the Table. The reaction was allowed to proceed with stirring for a minimum 4 hours, while monitoring the progress of the reaction periodically by GC-FID by removing small aliquots of the reaction mixture and injecting neat. Once the reaction was judged to be nearly complete, the reaction solution was filtered by syringe to remove suspended solids and the filtrate was submitted for GC-MS analysis to confirm tentative GC-FID peak assignments and identify the major products formed. This information was then used to calculate the GC yield of the desired alcohol addition products (sum of the HFE-Hydride+HFE-Olefin) and the Hydride/Olefin ratio. The results are summarized in the Table below and demonstrate that perfluorinated vinyl amines react with various alcohols generally in high yield to produce mainly the desired HFE-Hydrides, with the major byproduct being the corresponding HFE-Olefins. The HFE-Olefin byproducts are readily converted to the desired HFE-Hydride by treatment with anhydrous hydrogen fluoride as shown in the Examples above. Thus these reactions provide a high yield and selective route to HFE-Hydrides.

TABLE

Reactions of Perfluorinated Vinyl Amines with Various Alcohols

| Ex | PF-Vinylamine | mMoles | Alcohol | mMoles | $K_2CO_3$ (mMoles) | $CH_3CN$ Solvent (mLs) | Rxn Time (Hrs) | Reaction Temp °C. | GC Area % Yield of Desired * | Hydride/Olefin Ratio ** |
|---|---|---|---|---|---|---|---|---|---|---|
| 4 | 2-F-morpholine-N—CF=CF$_2$ | 3.22 | CF3CH2OH | 3.38 | 0.34 | 3 | 67 | 21 | 89 | 4.9 |
| 5 | 2-F-morpholine-N—CF=CF$_2$ | 3.22 | HCF2CF2CH2OH | 3.38 | 0.34 | 3 | 36 | 22 | 90 | 4.7 |
| 6 | 2-F-morpholine-N—CF=CF$_2$ | 3.22 | CF3CFHCF2CH2OH | 3.38 | 0.34 | 3 | 4 | 22 | 90 | 5.9 |
| 7 | 2-F-morpholine-N—CF=CF$_2$ | 3.22 | C2F5CH2OH | 3.38 | 0.34 | 3 | 4 | 22 | 94 | 4.8 |
| 8 | 2-F-morpholine-N—CF=CF$_2$ | 3.22 | (CF3)2CHOH | 3.38 | 0.34 | 3 | 4 | 22 | 90 | 3.7 |
| 9 | 2-F-morpholine-N—CF=CF$_2$ | 3.22 | CF3CFHCF2CH(CH3)OH | 3.38 | 0.34 | 3 | 4 | 22 | 96 | 1.4 |
| 10 | 2-F-morpholine-N—CF=CF$_2$ | 8.00 | HOCH2CF2CF2CH2OH | 4.00 | 0.60 | 3 | 18 | 40 | 74 | 1.1 |
| 11 | 2-F-morpholine-N—CF=CF$_2$ | 5.14 | CH2=CHCH2OH | 6.17 | 0.51 | 1 | 48 | 21 | 60 | No Olefin detected |
| 12 | 2-F-morpholine-N—CF=CF$_2$ | 5.14 | HC≡CCH2OH | 6.17 | 0.51 | 1 | 48 | 21 | 63 | No Olefin detected |
| 13 | 2-F-morpholine-N—CF=CF$_2$ | 5.14 | (CH3)2NCH2CH2OH | 6.17 | 0.51 | 1 | 24 | 21 | 57 | 15.9 |
| 14 | 2-F-morpholine-N—CF=CF$_2$ | 5.14 | HOCH2CH(CH2)2 | 6.17 | 0.51 | 1 | 24 | 21 | 85 | 7.6 |

TABLE-continued

Reactions of Perfluorinated Vinyl Amines with Various Alcohols

| Ex | PF-Vinylamine | mMoles | Alcohol | mMoles | K2CO3 (mMoles) | CH3CN Solvent (mLs) | Rxn Time (Hrs) | Reaction Temp °C. | GC Area % Yield of Desired * | Hydride/ Olefin Ratio ** |
|---|---|---|---|---|---|---|---|---|---|---|
| 15 | O(C4H8)N—CF=CF2 (morpholine-F) | 5.14 | HOCH2CH2OCH3 | 6.17 | 0.51 | 1 | 24 | 21 | 71 | 3.0 |
| 16 | O(C4H8)N—CF=CF2 | 5.14 | HO(CH2)2OH | 6.17 | 0.51 | 1 | 24 | 21 | 63 | 4.3 |
| 17 | O(C4H8)N—CF=CF2 | 6.43 | HOC2H4OC2H4OH | 3.06 | 0.60 | 5 | 18 | 21 | 40 | 3.3 |
| 18 | O(C4H8)N—CF=CF2 | 6.43 | HOCH2CH=CHCH2OH | 3.06 | 0.60 | 5 | 24 | 21 | 9 | No Olefin detected |
| 19 | (C2F5)2N—CF=CF2 | 3.22 | CH3OH | 6.50 | 0.34 | 3 | 92 | 21 | 76 | NA |
| 20 | (C2F5)2N—CF=CF2 | 3.22 | CH3CH2OH | 6.50 | 0.34 | 3 | 92 | 21 | 63 | 0.9 |
| 21 | (C2F5)2N—CF=CF2 | 3.22 | (CH3)2CHOH | 6.50 | 0.34 | 3 | 92 | 21 | 2 | NA |
| 22 | (C2F5)2N—CF=CF2 | 3.00 | HCF2CF2CH2OH | 3.30 | 0.30 | 3 | 18 | 21 | 84 | 1.4 |
| 23 | (C2F5)2N—CF=CF2 | 3.00 | CF3CH2OH | 3.30 | 0.30 | 3 | 19 | 21 | 85 | 1.6 |
| 24 | (C2F5)2N—CF=CF2 | 3.00 | (CF3)2CHOH | 3.30 | 0.30 | 3 | 21 | 21 | 79 | 0.9 |
| 25 | (C2F5)2N—CF=CF2 | 6.01 | HOC2H4OC2H4OH | 2.86 | 0.30 | 5 | 22 | 21 | 31 | 0.8 |
| 26 | (C2F5)2N—CF=CF2 | 6.01 | HOCH2CH=CHCH2OH | 2.86 | 0.30 | 5 | 40 | 21 | 11 | 0.9 |
| 27 | (C2F5)2N—CF=CF2 | 6.01 | HOC4H8OH | 2.86 | 0.30 | 5 | 22 | 21 | 21 | 0.6 |

TABLE-continued

Reactions of Perfluorinated Vinyl Amines with Various Alcohols

| Ex | PF-Vinylamine | mMoles | Alcohol | mMoles | K2CO3 (mMoles) | CH3CN Solvent (mLs) | Rxn Time (Hrs) | Reaction Temp °C. | GC Area % Yield of Desired * | Hydride/ Olefin Ratio ** |
|---|---|---|---|---|---|---|---|---|---|---|
| 28 | (CH3)2N—CF=CF2 | 3.20 | CH3OH | 4.70 | 0.40 | 4 | 24 | 21 | 73 | 5.6 |
| 29 | F3C—N(CF2—CF2)2N—CF=CF2 | 4.00 | CH3CH2OH | 4.00 | 0.41 | 4 | 24 | 21 | 87 | 2.9 |
| 30 | morpholino-N—CF=CF2 | 5.14 | HO(CH2)4OH | 6.17 | 0.51 | 1 | 24 | 21 | 29 | 1.9 |

* Based on conversion of PF-Vinylamine to desired HFE-Hydride (major) and HFE-Olefin (minor) addition products by GC-FID.
** HFE-Hydride to HFE-Olefin ratio determined from relative GC-FID peak areas.
NA means unable to quantify Hydride/Olefin ratio due to overlapping GC peaks.
Yields are unoptimized.
Yields reported for the difunctional alcohols, HOCH$_2$CF$_2$CF$_2$CH$_2$OH, HOCH$_2$CH$_2$OH, HOCH$_2$CH$_2$OCH$_2$CH$_2$OH, HOCH$_2$CH=CHCH$_2$OH, and HO(CH$_2$)$_4$OH are for the bis-addition products only.

Using the procedure and reagents described in Examples 4-30, the following hydrofluoroether (or HFE-Hydride) compounds were successfully prepared and characterized by GC-MS:

| Ex | Product |
|---|---|
| 4 | morpholino-N—CFHCF$_2$OCH$_2$CF$_3$ |
| 5 | morpholino-N—CFHCF$_2$OCH$_2$CF$_2$CF$_2$H |
| 6 | morpholino-N—CFHCF$_2$OCH$_2$CF$_2$CFHCF$_3$ |
| 7 | morpholino-N—CFHCF$_2$OCH$_2$C$_2$F$_5$ |
| 8 | morpholino-N—CFHCF$_2$OCH(CF$_3$)$_2$ |
| 9 | morpholino-N—CFHCF$_2$OCH(CH$_3$)CF$_2$CFHCF$_3$ |
| 10 | morpholino-N—CFHCF$_2$OCH$_2$CF$_2$CF$_2$CH$_2$OCF$_2$CFH—N-morpholino |
| 11 | morpholino-N—CFHCF$_2$OCH$_2$CH=CH$_2$ |
| 12 | morpholino-N—CFHCF$_2$OCH$_2$C≡C—H |
| 13 | perfluoromorpholino-C(F)(—)—C(F)(F)—O—CH$_2$CH$_2$—N(CH$_3$)$_2$ (with H on carbon) |
| 14 | perfluoromorpholino-C(F)(—)—C(F)(F)—O—CH$_2$-cyclopropyl (with H on carbon) |
| 15 | perfluoromorpholino-C(F)(—)—C(F)(F)—O—CH$_2$CH$_2$—O—CH$_3$ (with H on carbon) |

| Ex | Product |
|---|---|
| 16 | (structure: bis-perfluoromorpholine with ether linker) |
| 17 | (structure: bis-morpholine with triethylene glycol-type fluorinated linker) |
| 18 | (structure: bis-morpholine with fluorinated allylic ether linker) |
| 19 | (C$_2$F$_5$)$_2$N—CFHCF$_2$OCH$_3$ |
| 20 | (C$_2$F$_5$)$_2$N—CFHCF$_2$OCH$_2$CH$_3$ |
| 21 | (C$_2$F$_5$)$_2$N—CFHCF$_2$OCH(CH$_3$)$_2$ |
| 22 | (C$_2$F$_5$)$_2$N—CFHCF$_2$OCH$_2$CF$_2$CF$_2$H |
| 23 | (C$_2$F$_5$)$_2$N—CFHCF$_2$OCH$_2$CF$_3$ |
| 24 | (C$_2$F$_5$)$_2$N—CFCF$_2$OCH(CF$_3$)$_2$ |
| 25 | (C$_2$F$_5$)$_2$N—CFHCF$_2$—O—CH$_2$CH$_2$—O—CH$_2$CH$_2$—O—CF$_2$CFH—N(C$_2$F$_5$)$_2$ |
| 26 | (C$_2$F$_5$)$_2$N—CFHCF$_2$—O—CH$_2$CH=CHCH$_2$—O—CF$_2$CFH—N(C$_2$F$_5$)$_2$ |
| 27 | (C$_2$F$_5$)$_2$N—CFHCF$_2$—O—(CH$_2$)$_4$—O—CF$_2$CFH—N(C$_2$F$_5$)$_2$ |
| 28 | (F$_3$C)$_2$N—CFHCF$_2$OCH$_3$ |
| 29 | (perfluoropiperazine with F$_3$C— and —CFHCF$_2$OC$_2$H$_5$ substituents) |
| 30 | (perfluoromorpholine—CF$_2$CFH—O—(CH$_2$)$_4$—O—CFHCF$_2$—perfluoromorpholine) |

Example 31: Solubility of Various Solutes in 2,2,3,3,5,5,6,6-octafluoro-4-(1,2,2-trifluoro-2-methoxy-ethyl)morpholine Vs. Other Commercial HFE Solvents The maximum solubility of various solutes, including common lubricants and additives, was measured in 2,2,3,3,5,5,6,6-octafluoro-4-(1,2,2-trifluoro-2-methoxy-ethyl)morpholine solvent and compared with the solubility of the same solutes in two commercially available, non-flammable, HFE solvents, including a segregated HFE (Novec 7100) and a non-segregated HFE (PF-7600), both available from 3M Company, St. Paul Minn. The data was collected at room temperature and is summarized in the Table below. This data demonstrates that 2,2,3,3,5,5,6,6-octafluoro-4-(1,2,2-trifluoro-2-methoxy-ethyl)morpholine, a nitrogen-containing HFE-Hydride of the present invention, provides equivalent or superior solubility characteristics for many of the solutes tested and is an especially good solvent for relatively polar solutes.

TABLE

Solubility of Solutes in Fluorinated Solvents (Maximum Wt % Solute in Fluorinated Solvent)

| | | Fluorinated Solvent | | |
|---|---|---|---|---|
| Solutes | Solute Type | Ex #1 (morpholine-NCFHCF$_2$OCH$_3$) | PF-7600 (Comp) | Novec-7100 (Comp) |
| Fomblin Z-Dol | Perfluoropolyether lube | >10% | >10% | >10% |
| Fomblin Z-Tetraol | Perfluoropolyether lube | 1.8% | 1.0% | 0.3% |
| Moresco D40H | Perfluoropolyether lube | 1.5% | — | 0.5% |
| Dow Corning 556 | Methylphenylpolysiloxane | 8-11% * | 3-6% | Miscible |
| Dow Corning 200 (350cSt) | Polydimethylsiloxane | <0.8% | <0.2% | <0.3% |
| Mineral Oil White (Light) | Nonpolar Hydrocarbon | <0.5% | <0.2% | <0.2% |
| Dioctyl Phthalate | Polar Hydrocarbon | >30% | >30% | 5.4-5.8% |

\* Soluble at 50:50 wt ratio (50% by Wt) as well

Example 32: Solubility of 2,2,3,3,5,5,6,6-octafluoro-4-(1,2,2-trifluoro-2-methoxy-ethyl)morpholine and 2,2,3,3,5,5,6,6-octafluoro-4-[1,2,2-trifluoro-2-(2,2,3,3-tetrafluoropropoxy)ethyl]morpholine in Common Li Ion Battery Electrolyte Formulations Vs. Novec-7300

The maximum solubility of two nitrogen-containing HFE-Hydrides of the present invention was determined in a commonly employed carbonate-based solvent formulation (EC:EMC 3:7 by wt) used in lithium ion battery electrolytes and a similar electrolyte formulation containing 1.0M LiPF$_6$ (a commonly employed electrolyte salt). The solubility of these nitrogen-containing HFE-Hydrides in the two battery electrolyte formulations was compared to the solubility of Novec-7300, a commercially available segregated HFE that has been previously studied as a battery electrolyte cosolvent. The relative solubility data was collected at room temperature and is summarized in the Table below. This data demonstrates that the nitrogen containing HFE-Hydrides of the present invention have significantly better solubility in these relatively polar battery electrolyte formulations compared to Novec-7300. Thus, the nitrogen-containing HFE-Hydrides of the present invention represent promising battery electrolyte cosolvents that can provide improved formulation flexibility due to their enhanced solubility in commonly used electrolyte formulations.

TABLE

Solubility of HFE Cosolvents in LIB Electrolyte Formulations (Max Wt % HFE in electrolyte)

| HFE Cosolvent | EC:EMC 3:7 by Wt | 1.0M LiPF$_6$ in EC:EMC 3:7 by Wt |
|---|---|---|
| morpholine-NCFHCF$_2$OCH$_3$ (Ex #1) | >40% | 22% |
| morpholine-NCFHCF$_2$OCH$_2$CF$_2$CF$_2$H (Ex #2) | >40% | 55% |
| Novec-7300 (Comp) | <20% | 6% |

Example 33: Comparative Toxicity of 2,2,3,3,5,5,6,6-octafluoro-4-(1,2,2-trifluoro-2-methoxy-ethyl)morpholine Vs. Other Non-segregated HFEs The acute inhalation toxicity of 2,2,3,3,5,5,6,6-octafluoro-4-(1,2,2-trifluoro-2-methoxy-ethyl)morpholine in rats was determined by dosing animals at 5000 ppm for 4 hours followed by 14 day post-dose monitoring. Based on the animal test results and the vapor pressure (VP) of the test compound, the LC-50, No Observable Effect Level (NOEL), and the Acute Vapor Hazard Ratio were estimated. These values are summarized in the Table below and compared to other common non-segregated HFEs for which similar toxicity and vapor pressure (VP) data is available. In terms of these standard measures of toxicity, 2,2,3,3,5,5,6,6-octafluoro-4-(1,2,2-trifluoro-2-methoxy-ethyl)morpholine compares quite favorably to the other non-segregated HFEs and is among the least toxic materials tested.

TABLE

Comparative Toxicity of 2,2,3,3,5,5,6,6-octafluoro-4-(1,2,2-trifluoro-2-methoxy-ethyl)morpholine Vs. Other Non-segregated HFEs

| Compound | Structure | LC50 (LD50) data - inhalation | NOAEL/NOEL data | LC50 Value | VP (mmHg) at 25 C. | VP (atm) at 25 C. | Acute Vapor Hazard Ratio* |
|---|---|---|---|---|---|---|---|
| Ex #1 | $O(CF_2CF_2)NCFHCF_2OCH_3$ | LC50 >5000 ppm (rat, inhalation) - 3M | NOEL >5000 ppm (rat, inhalation) - 3M | 5000 | 15.8 | 0.0208 | 4 |
| OIME | $(CF_3)_2CHCF_2OCH_3$ | LC50 660 ppm (mouse, inhalation) - Daikin SDS | [NOAEL must be <660 ppm (mouse, inhalation) by inference] | 660 | 127.9 | 0.1683 | 255 |
| AE-3000 | $CF_3CH_2OCF_2CF_2H$ | LC50 3010 ppm (acute rat, inhal) - AGC SDS | NOEL 1000 ppm (90d inhalation) - AGC SDS NOEL <1500 ppm (rat inhalation, 1h) - 3M | 3010 | 233 | 0.3066 | 102 |
| 301-monohydride | $CF_3CFHCF_2OCH_3$ | LC50 >10,000 ppm (rat, inhal, 5d) - 3M | [NOAEL must be <10,000 ppm (rat inhal, 5d) by inference] | 10000 | 174 | 0.2289 | 23 |
| Novec 7600 | $CF_3CFHCF_2CH(CH_3)OCF_2CFHCF_3$ | LC50 (rat, inhalation, 4h), >2000 ppm - 3M | NOEL (rat, inhalation, 29d) <500 ppm | 2000 | 7 | 0.0092 | 5 |

*Vapor Hazard Ratio Reference:Popendorf, W., Am. Ind. Hyg. Assoc. J, 45 (10), 719-726, (1984)

Other embodiments of the invention are within the scope of the appended claims.

What is claimed is:

1. A working fluid comprising a hydrofluoroether compound, the hydrofluoroether compound represented by the following general formula (1):

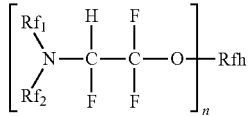

(1)

wherein n is 1-2, and each occurrence of $Rf_1$ and $Rf_2$ is:
  (i) independently a linear or branched perfluoroalkyl group having 1-8 carbon and optionally comprises one or more catenated heteroatoms; or
  (ii) bonded together to form a ring structure having 4-8 carbon atoms and optionally comprises one or more catenated heteroatoms; and
Rfh is, when n=1, a substituted or unsubstituted, monovalent, hydrocarbon group having 1-12 carbon atoms optionally comprising one or more catenary heteroatoms and, when n=2, a substituted or unsubstituted, divalent, hydrocarbon group having 1-12 carbon atoms optionally comprising one or more catenary heteroatoms,
  wherein the hydrofluoroether compound is present in the working fluid at an amount of at least 50% by weight based on the total weight of the working fluid.

2. The working fluid according to claim 1, wherein each occurrence of $Rf_1$ and $Rf_2$ is:
  (i) independently a linear or branched perfluoralkyl group having 1-4 carbons and optionally comprises one or more catenated heteroatoms; or (ii) bonded together to form a ring structure having 4-6 or carbon atoms and optionally comprises one or more catenated heteroatoms.

3. The working fluid according to claim 1, wherein Rfh is substituted with halogen atoms.

4. The working fluid according to claim 1, wherein Rfh is substituted with fluorine atoms.

5. The working fluid according to claim 1, wherein the hydrofluoroether compound has a degree of fluorination that is at least 60%.

6. A hydrofluoroether compound having one or more of the following formulas:

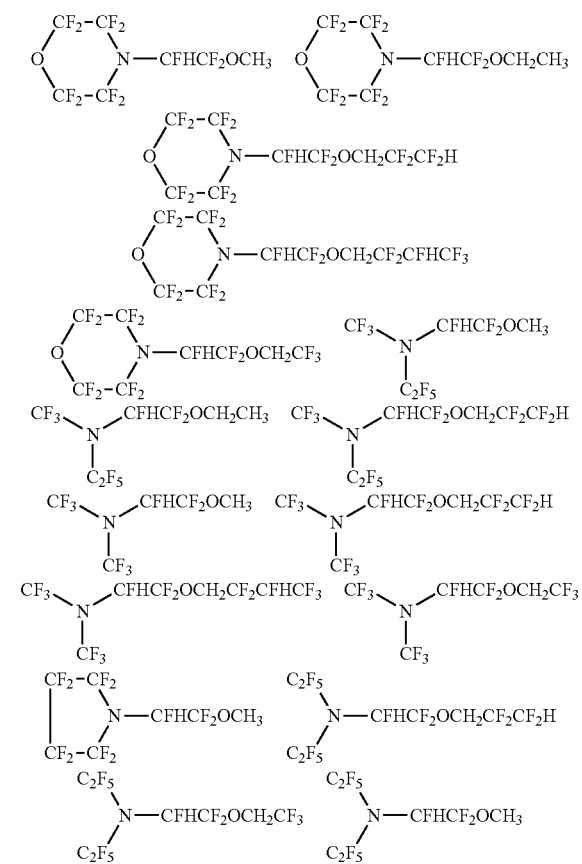

-continued

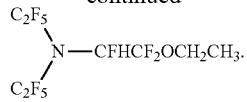

7. An apparatus for heat transfer comprising:
a device; and
a mechanism for transferring heat to or from the device, the mechanism comprising a heat transfer fluid that comprises a working fluid according to claim 1.

8. An apparatus for heat transfer according to claim 7, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

9. An apparatus for heat transfer according to claim 7, wherein the mechanism for transferring heat is a component in a system for maintaining a temperature or temperature range of an electronic device.

10. A method of transferring heat comprising:
providing a device; and
transferring heat to or from the device using a heat transfer fluid that comprises a working fluid according to claim 1.

\* \* \* \* \*

UNITED STATES PATENT AND TRADEMARK OFFICE
CERTIFICATE OF CORRECTION

PATENT NO. : 10,308,592 B2
APPLICATION NO. : 15/511259
DATED : June 4, 2019
INVENTOR(S) : William Lamanna Page 1 of 3

It is certified that error appears in the above-identified patent and that said Letters Patent is hereby corrected as shown below:

In the Specification

Column 5, Lines 25-33, Delete " 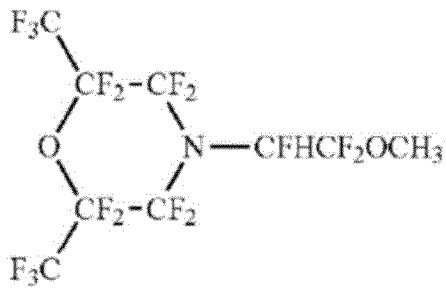 " and insert -- 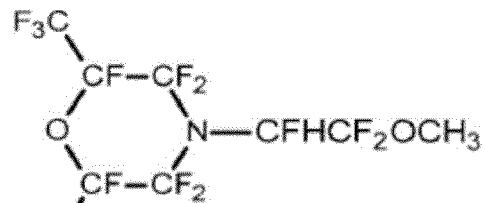 --, therefor.

Column 5, Lines 25-33, Delete " 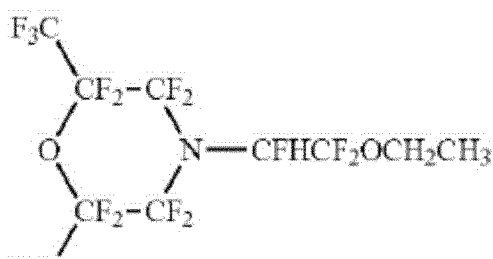 " and

Signed and Sealed this
Seventeenth Day of March, 2020

Andrei Iancu
*Director of the United States Patent and Trademark Office*

CERTIFICATE OF CORRECTION (continued)
U.S. Pat. No. 10,308,592 B2 insert -- 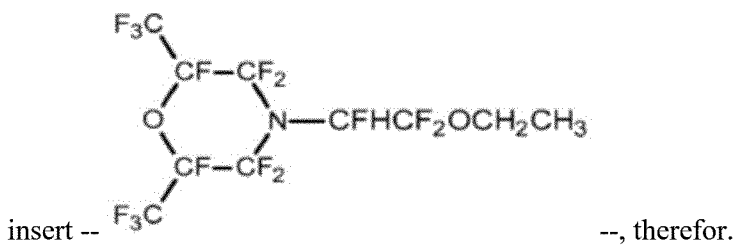 --, therefor.

Column 5, Lines 34-39, Delete " 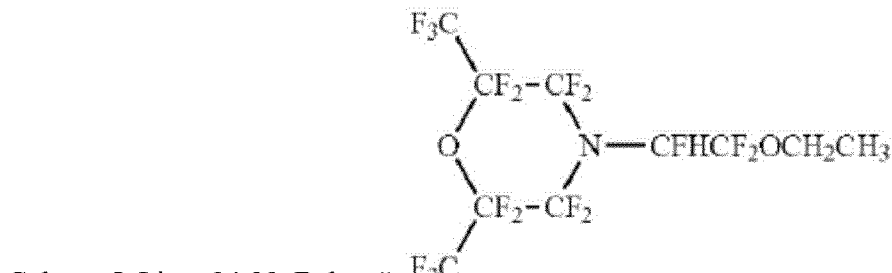 " and insert -- 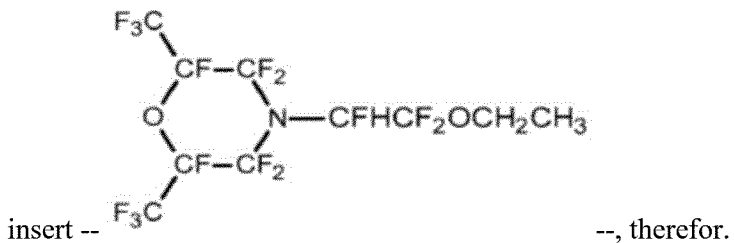 --, therefor.

Column 6, Lines 5-11, Delete " 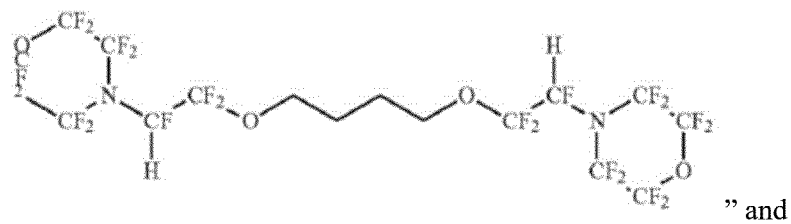 " and insert -- 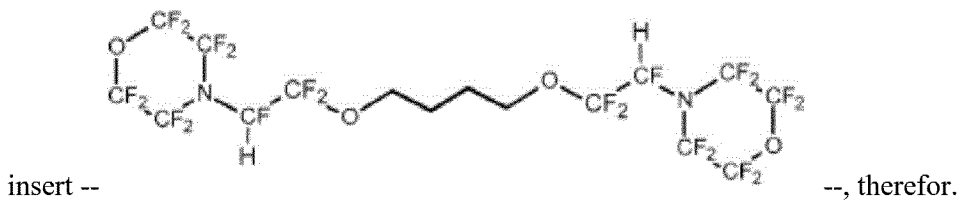 --, therefor.

Column 6, Lines 41-44, Delete "
$$GWP_i(t') = \frac{\int_0^{ITH} a_i[C(t)]\,dt}{\int_0^{ITH} a_{CO_2}[C_{CO_2}(t)]\,dt} = \frac{\int_0^{ITH} a_i C_{oi} e^{-t/\tau_i}\,dt}{\int_0^{ITH} a_{CO_2}[C_{CO_2}(t)]\,dt}$$
"

CERTIFICATE OF CORRECTION (continued)
U.S. Pat. No. 10,308,592 B2 and insert --
$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{t/\tau} dt}{\int_0^{ITH} a_{CO_2}[C_{CO_2}(t)]dt}$$
--, therefor.

Column 6, Line 46, Delete "a," and insert -- ai --, therefor.

Column 25, Line 35, Delete "reparatory" and insert -- separatory --, therefor.

Column 31-32, Line 5, Delete " 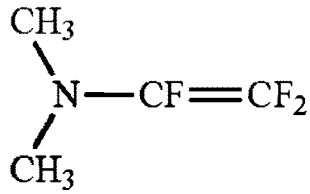 " and insert -- 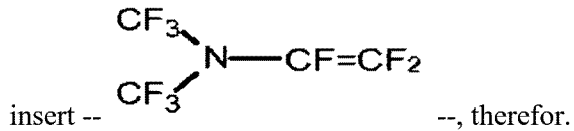 --, therefor.